United States Patent [19]

Doria et al.

[11] Patent Number: 4,482,555
[45] Date of Patent: Nov. 13, 1984

[54] SUBSTITUTED 1H-PYRAZOLO (1,5-a) PYRIMIDINES AND PROCESS FOR THEIR PREPARATION

[75] Inventors: Gianfederico Doria, Milan; Carlo Passarotti, Gallarate; Ada Buttinoni, Milan, all of Italy

[73] Assignee: Farmitalia Carlo Erba S.p.A., Milan, Italy

[21] Appl. No.: 474,205

[22] Filed: Mar. 10, 1983

[30] Foreign Application Priority Data

Mar. 16, 1982 [GB] United Kingdom ............... 8207637
Feb. 4, 1983 [GB] United Kingdom ............... 8303089

[51] Int. Cl.³ ............... C07D 487/04; A61K 31/495; A61K 31/41
[52] U.S. Cl. ............... 424/248.4; 544/117; 544/281; 424/251
[58] Field of Search ............... 544/281, 117; 424/251, 424/248.4

[56] References Cited

U.S. PATENT DOCUMENTS

| 3,907,799 | 9/1975 | O'Brien et al. | 544/281 |
| 3,920,652 | 11/1975 | Springer et al. | 544/281 |
| 3,925,385 | 12/1975 | O'Brien et al. | 544/281 |
| 4,093,617 | 6/1978 | Robins et al. | 544/281 |
| 4,129,738 | 12/1978 | Hoehn | 544/281 |
| 4,281,000 | 7/1981 | Dusza et al. | 544/281 |

OTHER PUBLICATIONS

Japanese Abstract 14424/66, 11/63.
Dutch Abstract 72/11011, 8/71.
Belgian Abstract 847698, 10/75.

Primary Examiner—Robert Gerstl
Assistant Examiner—Sharon A. Gibson
Attorney, Agent, or Firm—Murray, Whisenhunt and Ferguson

[57] ABSTRACT

Compounds of general formula (I)

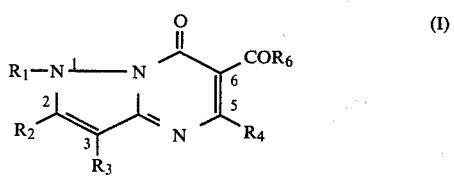

wherein
$R_1$ is a 2-pyridyl, 3-pyridyl or 4-pyridyl group; (b) a phenyl ring, unsubstituted or substituted by one or two groups chosen from halogen, trihalo-$C_1$-$C_4$ alkyl, $C_1$-$C_6$ alkyl, nitro, amino and $C_2$-$C_6$ alkanoylamino; (c) benzyl; or (d) $C_1$-$C_6$ alkyl;
each of $R_2$ and $R_3$ independently is a hydrogen or a halogen atom or $C_1$-$C_6$ alkyl;
$R_4$ is hydrogen, $C_1$-$C_6$ alkyl or phenyl;
$R_5$ is (a')

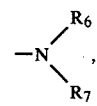

wherein each of $R_6$ and $R_7$ independently is hydrogen or $C_1$-$C_6$ alkyl, or $R_6$ and $R_7$, taken together with the nitrogen atom to which they are linked, form a morpholino, piperidino, N-pyrrolidinyl or N-piperazinyl ring, wherein the N-piperazinyl ring is unsubstituted or substituted by $C_1$-$C_6$ alkyl;
(b') a

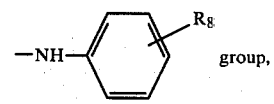

wherein $R_8$ is hydrogen, $C_1$-$C_4$ alkyl, $C_1$-$C_4$ alkoxy or halogen;
(c') —$NHR_9$, wherein $R_9$ is a 2-pyridyl, 3-pyridyl, 4-pyridyl, 2-pyrimidinyl, 2-pyrazinyl, 3-pyrazolyl, 2-thiazolyl or 2-benzothiazolyl group, each of these groups being unsubstituted or substituted by one or two groups chosen from halogen, $C_1$-$C_6$ alkyl, phenyl, hydroxy and $C_1$-$C_6$ alkoxy;
(d')

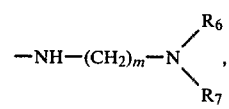

wherein m is 1, 2 or 3 and
$R_6$ and $R_7$ are as defined above; or the pharmaceutically acceptable salts thereof; are disclosed as antiinflammatory agents.

10 Claims, No Drawings

SUBSTITUTED 1H-PYRAZOLO (1,5-A) PYRIMIDINES AND PROCESS FOR THEIR PREPARATION

The present invention relates to new substituted 1H-pyrazolo[1,5-a]pyrimidines, to a process for their preparation and to pharmaceutical compositions containing them. The invention provides compounds having the following general formula (I)

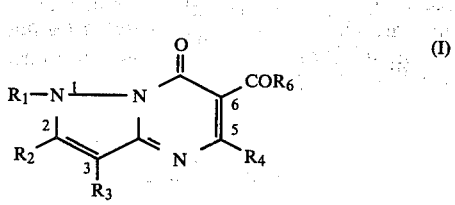

wherein $R_1$ is (a) a pyridyl group, unsubstituted or substituted by a $C_1$-$C_6$ alkyl group; (b) a phenyl ring, unsubstituted or substituted by one or more substituents chosen from halogen, trihalo-$C_1$-$C_4$ alkyl, $C_1$-$C_6$ alkyl, $C_1$-$C_6$ alkoxy, hydroxy, formyloxy, $C_2$-$C_6$ alkanoyloxy, nitro, amino, formylamino and $C_2$-$C_6$ alkanoylamino; (c) benzyl; or (d) $C_1$-$C_6$ alkyl;

each of $R_2$ and $R_3$ independently is a hydrogen or a halogen atom or $C_1$-$C_6$ alkyl;

$R_4$ is hydrogen, $C_1$-$C_6$ alkyl or phenyl;

$R_5$ is (a')

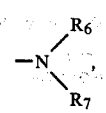

wherein each of $R_6$ and $R_7$ independently is hydrogen or $C_1$-$C_6$ alkyl, or $R_6$ and $R_7$, taken together with the nitrogen atom to which they are linked, form a morpholino, piperidino, N-pyrrolidinyl or N-piperazinyl ring, all the rings being unsubstituted or substituted by $C_1$-$C_6$ alkyl; (b')

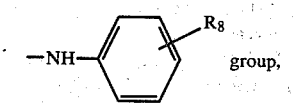

wherein $R_8$ is hydrogen, $C_1$-$C_4$ alkyl, $C_1$-$C_4$ alkoxy or halogen;

(c') a —NH—$R_9$ group, wherein $R_9$ is an unsaturated heterocyclic ring containing one or two heteroatoms chosen from nitrogen and sulphur, unsubstituted or substituted by one or two substituents chosen from halogen, $C_1$-$C_6$ alkyl, $C_1$-$C_6$ alkoxy, hydroxy and phenyl;

(d')

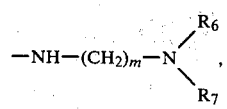

wherein m is 1, 2 or 3 and $R_6$ and $R_7$ are as defined above; or (e') hydroxy or $C_1$-$C_6$ alkoxy unsubstituted or substituted by

wherein $R_6$ and $R_7$ are as defined above; and wherein $R_5$ is not as defined above under (e') when $R_1$ is $C_1$-$C_6$ alkyl; and the pharmaceutically acceptable salts thereof.

The present invention includes also the metabolites and the metabolic precursors of the compounds of formula (I) and all the possible isomers of the compounds of formula (I), e.g. optical isomers, and the mixtures thereof. The alkyl, alkoxy, alkoxycarbonyl, alkanoyloxy and alkanoylamino groups may be branched or straight chain groups. A halogen atom is, for example, chlorine, bromine or fluorine, preferably it is chlorine or bromine.

A trihalo-$C_1$-$C_4$ alkyl group may be, for example, a trifluoro-$C_1$-$C_4$ alkyl group, preferably it is trifluoromethyl. A $C_2$-$C_6$ alkanoyloxy group is, for example, acetoxy, propionyloxy, butyryloxy or valeryloxy, preferably it is acetoxy.

A $C_1$-$C_6$ alkyl group is preferably a $C_1$-$C_4$ alkyl group, in particular, methyl, ethyl, propyl or tert.butyl. A $C_1$-$C_6$ alkoxy group is preferably $C_1$-$C_4$ alkoxy, in particular, methoxy, ethoxy, propoxy or butoxy. A $C_2$-$C_6$ alkanoylamino group is, for example, acetylamino, propionylamino, butyrylamino or valerylamino, preferably it is acetylamino.

When $R_1$ is a $C_1$-$C_6$ alkyl group, it is, for example, methyl, ethyl, propyl, isopropyl, butyl, isobutyl or tert-butyl, preferably it is methyl, ethyl, propyl or tert-butyl. When $R_1$ is a pyridyl group substituted by a $C_1$-$C_6$ alkyl group, the alkyl group may be, for example, methyl, ethyl or propyl, preferably it is methyl. When $R_1$ is a phenyl ring substituted as defined above, it is preferably substituted by one or more substituents chosen from chlorine, fluorine, trifluoromethyl, methyl, methoxy, amino and acetylamino. When $R_2$ and/or $R_3$ is a halogen atom it is, e.g., chlorine, bromine or fluorine, preferably it is chlorine or bromine. When $R_2$ and/or $R_3$ represents a $C_1$-$C_6$ alkyl group, it is, for example, methyl, ethyl, propyl or isopropyl, preferably it is methyl. When $R_4$ represents a $C_1$-$C_6$ alkyl group, it is, for example, methyl, ethyl, propyl, isopropyl or butyl, preferably it is methyl, ethyl, propyl or isopropyl.

When one or both of $R_6$ and $R_7$, being the same or different, is a $C_1$-$C_6$ alkyl group, it is for example methyl, ethyl, propyl, isopropyl or butyl, preferably it is methyl, ethyl, propyl or isopropyl.

When $R_6$ and $R_7$, taken together with the nitrogen atom to which they are linked, form a morpholino, piperidino, N-pyrrolidinyl or N-piperazinyl ring and said ring is substituted by $C_1$-$C_6$ alkyl, the alkyl group is preferably $C_1$-$C_4$ alkyl, in particular methyl or ethyl. When $R_8$ is halogen, it is, e.g., chlorine, bromine or fluorine, preferably it is chlorine or bromine.

When $R_8$ is a $C_1$-$C_4$ alkyl group, it is preferably a methyl group. When $R_8$ is a $C_1$-$C_4$ alkoxy group, it is preferably methoxy or ethoxy. When $R_9$ is a heterocyclic ring as defined above under (c'), it may be a heteromonocyclic or heterobicyclic ring, preferably it is a pyridyl, a pyrimidinyl, a thiazolyl, a pyrazolyl or a benzothiazolyl group, each of them being preferably unsubstituted or substituted by one or two substituents chosen from methyl, chlorine, bromine and methoxy.

Preferred compounds of the invention are those of formula (I) wherein $R_1$ is pyridyl; benzyl; $C_1$–$C_6$ alkyl; or phenyl unsubstituted or substituted by one or two substituents chosen from chlorine, methyl, amino and acetylamino;

each of $R_2$ and $R_3$ independently represents hydrogen, chlorine or a methyl group;

$R_4$ is hydrogen, $C_1$–$C_2$ alkyl or phenyl;

$R_5$ is (a'')

wherein each of $R_6'$ and $R_7'$ is independently hydrogen or $C_1$–$C_4$ alkyl; or $R_6'$ and $R_7'$, taken together with the nitrogen atom to which they are linked, form a morpholino, piperidino or N-piperazinyl ring, wherein the N-piperazinyl ring is unsubstituted or substituted by $C_1$–$C_4$ alkyl;

(b'')

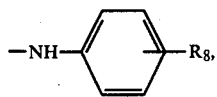

wherein $R_8$ is hydrogen, methyl, methoxy or chlorine;

(c'') —NHR$_9$, wherein R$_9$ is a pyridyl, pyrimidinyl, 2-thiazolyl or 2-benzothiazolyl group, wherein all the groups are unsubstituted or substituted by one or two substituents chosen from chlorine, bromine, methyl and methoxy; or (d'')

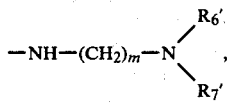

wherein m, $R_6'$ and $R_7'$ are as defined above; and the pharmaceutically acceptable salts thereof.

More preferred compounds of the invention are those of formula (I) wherein:

$R_1$ pyridyl; benzyl; or phenyl unsubstituted or substituted by one or two substitutents chosen from chlorine, methyl, amino and acetylamino;

each of $R_2$ and $R_3$ independently represents hydrogen, chlorine or a methyl group;

$R_4$ is hydrogen, $C_1$–$C_2$ alkyl or phenyl;

$R_5$ is (a'')

wherein each of $R_6''$ and $R_7''$ is independently hydrogen or $C_1$–$C_3$ alkyl, or $R_6''$ and $R_7''$ taken together with the nitrogen atom to which they are linked, form a morpholino, a piperidino or a N-piperazinyl ring, wherein the N-piperazinyl ring is unsubstituted or substituted by $C_1$–$C_4$ alkyl;

(b'')

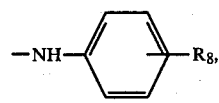

wherein $R_8$ is hydrogen, methyl, methoxy or chlorine;

(c'') —NHR$_9$, wherein R$_9$ is a pyridyl, pyrimidinyl, 2-thiazolyl or 2-benzothiazolyl group wherein all the groups are unsubstituted or substituted by one or two substitutents chosen from chlorine, bromine, methyl and methoxy; or (d'')

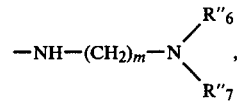

wherein m, $R_6''$ and $R_7''$ are as defined above; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine β-phenethylamine, N-benzyl-β-phenethylamine, N-benzyl-N,N-dimethylamine and the other acceptable organic amines, as well as the salts with inorganic acids, e.g. nitric, hydrochloric, hydrobromic and sulphuric acids and with organic acids, e.g. citric, tartaric, maleic, malic, fumaric, methanesulphonic and ethanesulphonic acids.

Examples of particularly preferred compounds of the invention are:

1-phenyl-7-oxo-1H,7H-pyrazolo[1,5-a]pyrimidine-6-N-(3-pyridyl)-carboxamide;

1-phenyl-7-oxo-1H,7H-pyrazolo[1,5-a]pyrimidine-6-N-(2-pyridyl)-carboxamide;

1-phenyl-7-oxo-1H,7H-pyrazolo[1,5-a]pyrimidine-6-N-(6-methyl-2-pyridyl)-carboxamide;

1-phenyl-7-oxo-1H,7H-pyrazolo[1,5-a]pyrimidine-6-N-(5-chloro-2-pyridyl)-carboxamide;

1-phenyl-7-oxo-1H,7H-pyrazolo[1,5-a]pyrimidine-6-N-(2-pyrimidinyl)-carboxamide;

3-methyl-1-phenyl-7-oxo-1H,7H-pyrazolo[1,5-a]pyrimidine-6-N-(2-pyridyl)-carboxamide;

1-phenyl-7-oxo-1H,7H-pyrazolo[1,5-a]pyrimidine-6-N-(6-methoxy-3-pyridyl)-carboxamide;

5-methyl-1-phenyl-7-oxo-1H,7H-pyrazolo[1,5-a]pyrimidine-6-N-(2-pyridyl)-carboxamide;

5-methyl-1-phenyl-7-oxo-1H,7H-pyrazolo[1,5-a]pyrimidine-6-N-(2-pyrimidinyl)-carboxamide;

3,5-dimethyl-1-phenyl-7-oxo-1H,7H-pyrazolo[1,5-a]pyrimidine-6-N-(2-pyridyl)-carboxamide;

5-ethyl-1-phenyl-7-oxo-1H,7H-pyrazolo[1,5-a]pyrimidine-6-N-(2-pyridyl)-carboxamide;

1-(3-chloro-phenyl)-7-oxo-1H,7H-pyrazolo[1,5-a]pyrimidine-6-N-(2-pyridyl)-carboxamide;

1-(3-chloro-phenyl)-5-methyl-7-oxo-1H,7H-pyrazolo[1,5-a]pyrimidine-6-N-(2-pyridyl)-carboxamide;

1-(4-chloro-phenyl)-7-oxo-1H,7H-pyrazolo[1,5-a]pyrimidine-6-N-(2-pyridyl)-carboxamide;

1-(4-chloro-phenyl)-5-methyl-7-oxo-1H,7H-pyrazolo[1,5-a]pyrimidine-6-N-(2-pyridyl)-carboxamide;

1-(4-amino-phenyl)-7-oxo-1H,7H-pyrazolo[1,5-a]pyrimidine-6-N-(2-pyridyl)-carboxamide;

1-(4-acetylamino-phenyl)-7-oxo-1H,7H-pyrazolo[1,5-a]pyrimidine-6-N-(2-pyridyl)-carboxamide;

1-(3-pyridyl)-7-oxo-1H,7H-pyrazolo[1,5-a]pyrimidine-6-N-(2-pyridyl)-carboxamide;

1-(3-pyridyl)-7-oxo-1H,7H-pyrazolo[1,5-a]pyrimidine-6-N-(6-methyl-2-pyridyl)-carboxamide;

5-methyl-1-(3-pyridyl)-7-oxo-1H,7H-pyrazolo[1,5-a]pyrimidine-6-N-(2-pyridyl)-carboxamide;

1-(3-pyridyl)-7-oxo-1H,7H-pyrazolo[1,5-a]pyrimidine-6-N-(5-chloro-2-pyridyl)-carboxamide;

1-(3-pyridyl)-7-oxo-1H,7H-pyrazolo[1,5-a]pyrimidine-6-N-(2-thiazolyl)-carboxamide;

1-(2-pyridyl)-7-oxo-1H,7H-pyrazolo[1,5-a]pyrimidine-6-N-(5-chloro-2-pyridyl)-carboxamide;

5-methyl-1-(2-pyridyl)-7-oxo-1H,7H-pyrazolo[1,5-a]pyrimidine-6-N-(2-thiazolyl)-carboxamide;

1-benzyl-7-oxo-1H,7H-pyrazolo[1,5-a]pyrimidine-6-N-(2-pyridyl)-carboxamide;

1-benzyl-5-methyl-7-oxo-1H,7H-pyrazolo[1,5-a]pyrimidine-6-N-(2-pyridyl)-carboxamide;

1-phenyl-7-oxo-1H,7H-pyrazolo[1,5-a]pyrimidine-6-N-(2-piperidino-ethyl)-carboxamide;

1-methyl-7-oxo-1H,7H-pyrazolo[1,5-a]pyrimidine-6-N-(2-pyridyl)-carboxamide;

1-ethyl-7-oxo-1H,7H-pyrazolo[1,5-a]pyrimidine-6-N-(2-pyridyl)-carboxamide;

1-(2-pyridyl)-7-oxo-1H,7H-pyrazolo[1,5-a]pyrimidine-6-N-(2-pyridyl)-carboxamide;

1-methyl-7-oxo-1H,7H-pyrazolo[1,5-a]pyrimidine-6-N-(2-thiazolyl)-carboxamide;

1-methyl-7-oxo-1H,7H-pyrazolo[1,5-a]pyrimidine-6-N-(2-benzothiazolyl)-carboxamide;

1-(2-pyridyl)-7-oxo-1H,7H-pyrazolo[1,5-a]pyrimidine-6-N-(2-thiazolyl)-carboxamide;

1-(2-pyridyl)-7-oxo-1H,7H-pyrazolo[1,5-a]pyrimidine-6-N-(2-benzothiazolyl)-carboxamide;

1-methyl-7-oxo-1H,7H-pyrazolo[1,5-a]pyrimidine-6-N-(2-piperidino-ethyl)-carboxamide;

1,5-dimethyl-7-oxo-1H,7H-pyrazolo[1,5-a]pyrimidine-6-N-(2-pyridyl)-carboxamide;

1-(4-pyridyl)-7-oxo-1H,7H-pyrazolo[1,5-a]pyrimidine-6-N-(2-pyridyl)-carboxamide;

1-methyl-7-oxo-1H,7H-pyrazolo[1,5-a]pyrimidine-6-N-(5-chloro-2-pyridyl)-carboxamide;

5-methyl-1-(2-pyridyl)-7-oxo-1H,7H-pyrazolo[1,5-a]pyrimidine-6-N-(2-pyridyl)-carboxamide;

1-phenyl-7-oxo-1H,7H-pyrazolo[1,5-a]pyrimidine-6-carboxylic acid;

5-methyl-1-phenyl-7-oxo-1H,7H-pyrazolo[1,5-a]pyrimidine-6-carboxylic acid;

1-(3-pyridyl)-7-oxo-1H,7H-pyrazolo[1,5-a]pyrimidine-6-carboxylic acid; and 5-methyl-1-(3-pyridyl)-7-oxo-1H,7H-pyrazolo[1,5-a]pyrimidine-6-carboxylic acid; and the pharmaceutically acceptable salts thereof.

The compounds of the invention can be prepared by a process comprising:

(a) cyclizing a compound of formula (II)

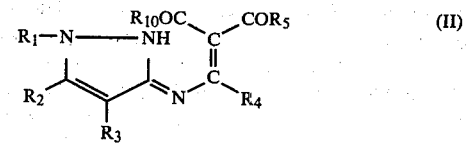

wherein $R_1$, $R_2$, $R_3$, $R_4$ and $R_5$ are as defined above and $R_{10}$ is a nucleophile group able to easily remove the proton linked to the nitrogen atom of the pyrazolyl ring, or a salt thereof; or (b) reacting a compound of formula (III)

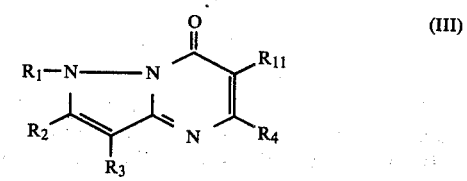

wherein $R_1$, $R_2$, $R_3$ and $R_4$ are as defined above and $R_{11}$ is a free or esterified carboxy group, or a salt thereof, with a compound of formula (IV)

$$H_2N-R_9 \qquad (IV)$$

wherein $R_9$ is as defined above, or an active derivative thereof, so obtaining compounds of formula (I) wherein $R_5$ is as defined above under (c'); or (c) reacting a compound of formula (V)

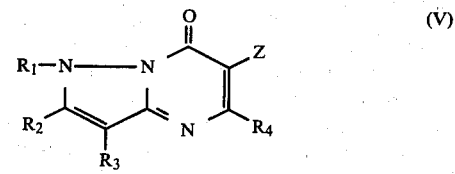

wherein $R_1$, $R_2$, $R_3$ and $R_4$ are as defined above and Z is a reactive carboxy group, with a compound of formula (VI)

or of formula (VII)

or of formula (VIII)

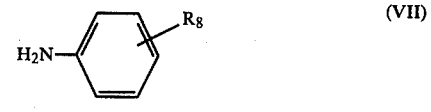

wherein $R_6$, $R_7$, $R_8$ and m are as defined above, so obtaining compounds of formula (I) wherein $R_5$ is as defined above under (a'), (b') and (d') respectively, and if desired, converting a compound of formula (I) into another compound of formula (I) and/or, if desired, converting a compound of formula (I) into a pharmaceutically acceptable salt thereof and/or, if desired, obtaining a free compound of formula (I) from a salt thereof and/or, if desired, separating a mixture of isomers into the single isomers.

When $R_{10}$ is a nucleophile group as defined above, it is, for example, hydroxy, tri-($C_1$-$C_6$)alkyl-silyloxy, or $C_1$-$C_6$ alkoxy unsubstituted or substituted by a

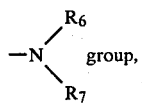 group, wherein $R_6$ and $R_7$ are as defined above.

The compounds of formula (II) may also be represented by the tautomeric formula (IIa)

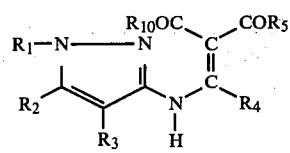 (IIa)

wherein $R_1$, $R_2$, $R_3$, $R_4$, $R_5$ and $R_{10}$ are as defined above.

Preferred salts of the compounds of formula (II) and (III) are, for example, those with inorganic acids such as hydrochloric, hydrobromic, hydroiodic, phosphoric and sulphuric acid.

The cyclization of a compound of formula (II) may be, for example, carried out by treatment with an acid condensing agent such as polyphosphoric acid (alone or in the presence of phosphorus oxychloride), sulphuric acid, hydrochloric acid, methanesulphonic acid or p-toluenesulphonic acid, at a temperature ranging preferably about between 50° C. and 150° C.; the reaction may be carried out in an organic solvent such as dimethylformamide, dimethylacetamide, dimethylsulphoxide, benzene, toluene, xylene, ethylene glycol monomethylether or dichloroethane, but it is preferably carried out in the absence of a solvent.

Alternatively, the cyclization of a compound of formula (II) may be carried out by heating the compound at a temperature ranging between about 150° C. and about 350° C., preferably between 200° C. and 300° C., in an inert high boiling organic solvent such as diphenyl ether, or in the absence of a solvent.

When in a compound of formula (III) $R_{11}$ is an esterified carboxy group, it is, for example, an alkoxy-carbonyl group or a tri-($C_1$-$C_6$)alkyl-silyloxy-carbonyl group.

The reaction between a compound of formula (III), or a salt thereof, and a compound of formula (IV) may be carried out, for example, by heating with polyphosphoric or methanesulphonic or p-toluenesulphonic acid at a temperature varying between about 50° C. and about 200° C. in the absence of a solvent or in the presence of an inert organic solvent such as dimethylformamide, dimethylacetamide, toluene or xylene; or, alternatively, by heating from about 50° C. to about 150° C. without any acidic agent and in the presence of an organic solvent only, e.g., toluene or xylene, if required.

An active derivative of a compound of formula (IV) is, e.g., a compound obtained by reacting a compound of formula (IV) with $PCl_3$ in pyridine, at a temperature ranging from room temperature and about 50° C. The reaction between such active derivative of a compound of formula (IV) and a free acid of formula (III) is carried out in the same medium by heating to a temperature ranging from about 50° C. to the reflux temperature.

The reactive carboxy group Z in a compound of formula (V) is, for example, a —COZ' group, wherein Z' is, e.g., halogen, preferably chlorine or bromine, or Z is a —COOCOOR$_{12}$ group, wherein $R_{12}$ is, e.g., $C_1$-$C_6$ alkyl, phenyl or benzyl. The reaction between a compound of formula (V) and a compound of formula (VI), (VII) or (VIIi) may be carried out, for example, in an inert organic solvent such as benzene, toluene, xylene, dioxane, chloroform, dichloroethane, methylene chloride or tetrahydrofuran, at a temperature varying between about 0° C. and about 120° C., preferably in the presence of a base such as triethylamine or pyridine. A compound of formula (I) may be converted, as stated above, into another compound of formula (I) by known methods. For example, a compound of formula (I) wherein —COR$_5$ is $C_1$-$C_6$ alkoxy-carbonyl, wherein the alkoxy group is unsubstituted or substituted by a

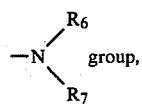 group, wherein $R_6$ and $R_7$ are as defined above, may be converted into a compound of formula (I) wherein —COR$_5$ is a free carboxy group by conventional methods, for example by acid hydrolysis using, for example, HCl, HBr, HI in water or in acetic acid or dioxane or their mixtures and operating at a temperature ranging from the room temperature to about 150° C.; the same hydrolysis may be also carried out e.g. by treatment with lithium bromide in dimethylformamide at a temperature higher than 50° C.

Furthermore, for example, a compound of formula (I) wherein —COR$_5$ is a free carboxy group may be converted into a compound of formula (I) wherein

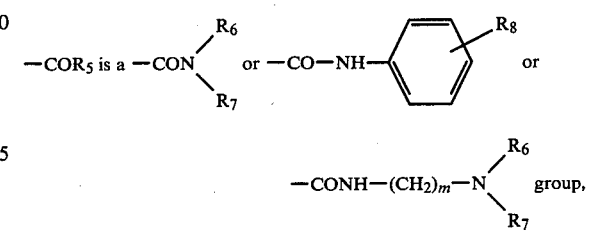

wherein $R_6$, $R_7$, $R_8$ and m are as defined above, by converting the carboxylic acid into the corresponding halocarbonyl, preferably chlorocarbonyl, derivative, by reaction, e.g., with the desired acid halide, for example oxalyl chloride, thionyl chloride, $PCl_3$, $PCl_5$ or $POCl_3$, either in the absence of solvents or in an inert organic solvent such as benzene, toluene, xylene, dioxane, dichloroethane, methylene chloride or tetrahydrofuran, at a temperature ranging preferably from about 0° C. to about 120° C., and then reacting the obtained halocarbonyl derivative with a compound of formula

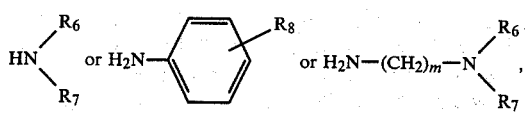

wherein $R_6$, $R_7$, $R_8$ and m are as defined above, according to the same reaction conditions described above for the reaction of a compound of formula (V) with a compound of formula (VI), (VII), or (VIII).

A compound of formula (I), wherein $-COR_5$ is carboxy or a $C_1-C_6$ alkoxycarbonyl group, wherein the alkoxy group is unsubstituted or substituted by a

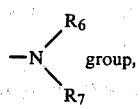

group, may be converted into a compound of formula (I), wherein $-COR_5$ is a $-CONH-R_9$ group, wherein $R_9$ is as defined above, by reaction with a compound of formula $NH_2R_9$, wherein $R_9$ is as defined above, by following, for example, the same reaction conditions described above for the reaction of a compound of formula (III) with a compound of formula (IV).

Furthermore, for example, a compound of formula (I), wherein $-COR_5$ is a free carboxy group, may be converted into a compound of formula (I) wherein $-COR_5$ is $C_1-C_6$ alkoxy-carbonyl, unsubstituted or substituted by a

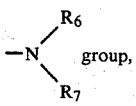

group, wherein $R_6$ and $R_7$ are as defined above, by conventional methods, for example, by converting the carboxylic acid into the corresponding chlorocarbonyl derivative, following, e.g., one of experimental methods described above and then reacting the obtained chlorocarbonyl derivative with an alcohol of formula (IX)

$$R'_5-OH \qquad (IX)$$

wherein $R'_5$ is a $C_1-C_6$ alkyl group unsubstituted or substituted by a

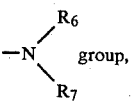

wherein $R_6$ and $R_7$ are as defined above, in the absence of a solvent or in the presence of an inert organic solvent such as benzene, toluene, dioxane, tetrahydrofuran at a temperature varying between about 0° C. and about 120° C.

Furthermore, for example, a nitro group as substituent in the $R_1$ phenyl group may be converted into an amino group by treatment, for example, with stannous chloride in concentrated hydrochloric acid, using, if necessary, an organic cosolvent such as acetic acid, dioxane, tetrahydrofuran at a temperature varying between room temperature and about 100° C.

Furthermore, for example, an amino or hydroxy group may be converted respectively into a formylamino, $C_2-C_6$ alkanoylamino or $C_2-C_6$ alkanoyloxy group, for example by reaction with formic acid or with the corresponding alkanoyl anhydride without any solvent or in an organic solvent such as dioxane, dimethylformamide, tetrahydrofuran, usually in the presence of a base such as pyridine or triethylamine at a temperature varying between 0° C. and about 100° C.

Also the optional salification of a compound of formula (I) as well as the conversion of a salt into a free compound and the separation of a mixture of isomers into the single isomers may be carried out by conventional methods.

For example, the separation of a mixture of optical isomers into the individual isomers may be carried out by salification with an optically active base or acid and subsequent fractional crystallization.

The compounds of formula (II) may be prepared, for example, by reacting a compound of formula (X)

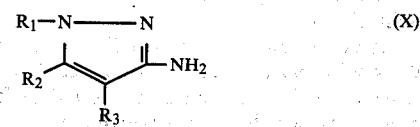

wherein $R_1$, $R_2$ and $R_3$ are as defined above, or a salt thereof, with a compound of formula (XI)

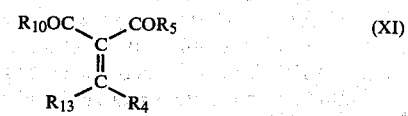

wherein $R_4$, $R_5$ and $R_{10}$ are as defined above and $R_{13}$ is a reactive group chosen, preferably, from hydroxy, amino, $C_1-C_6$ alkoxy or tri-$(C_1-C_6)$alkyl-silyloxy.

Preferred salts of a compounds of formula (X) are, for example, those with inorganic acids such as hydrochloric, hydrobromic, phosphoric and sulphuric acid.

The reaction between a compound of formula (X) and a compound of formula (XI) may be carried out, for example, by heating in solvents such as dioxane, toluene, xylene, acetonitrile, $C_1-C_4$ alkyl alcohols, acetic acid, dimethylformamide, dimethylacetamide, diphenylether or in the absence of a solvent at a temperature varying from about 50° C. to about 200° C. Preferably, when $R_{10}$ is hydroxy, the reaction between a compound of formula (X) and a compound of formula (XI) is carried out in the presence of an acid condensing agent such as polyphosphoric acid, methanesulphonic acid, p-toluenesulphonic acid or acetic acid using the same experimental conditions, as described above, for the cyclization of the compounds of formula (II).

Under these specific conditions the reaction of a compound of formula (X) with a compound of formula (XI) may be carried out till a compound of formula (I) is obtained without the need to isolate the intermediate product of formula (II) formed during the reaction.

The compounds of formula (III), wherein $R_1$ is $C_1-C_6$ alkyl, are compounds of formula (I) which are excluded from the scope of the invention, as stated above.

The compounds of formula (III) may be prepared by cyclizing a compound of formula (XII)

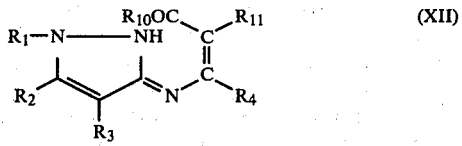

wherein $R_1$, $R_2$, $R_3$, $R_4$, $R_{10}$ and $R_{11}$ are as defined above, using the same experimental conditions specified above for the cyclization of a compound of formula (II).

Alternatively, for example, the compounds of formula (III), wherein $R_{11}$ is a free carboxy group, may be prepared by hydrolyzing a compound of formula (III) wherein $R_{11}$ is an esterified carboxy group or a tri-($C_1$–$C_6$)alkyl-silyloxy-carbonyl group, by treatment, for example, with a mineral acid such as HCl, HBr, HI in water or in acetic acid or dioxane or their mixtures at a temperature varying between room temperature and about 120° C.

The compounds of formula (V), wherein Z' is halogen, preferably chlorine or bromine, may be prepared, for example, by reacting a compound of formula (III), wherein $R_{11}$ is a free carboxy group, with a suitable acid halide such as oxalyl chloride, $SOCl_2$, $PCl_3$, $POCl_3$, $PBr_3$, for example, in a solvent such as benzene, toluene, dioxane, dichloroethane, at a temperature varying between room temperature and about 120° C.

The compounds of formula (V), wherein Z is a group —COOCOOR$_{12}$, wherein $R_{12}$ is as defined above, may be prepared, for example, by reacting a compound of formula (III), wherein $R_{11}$ is a free carboxy group, with a compound of formula YCOOR$_{12}$, wherein $R_{12}$ is as defined above and Y is a halogen atom, preferably chlorine or bromine, in a solvent such as benzene, toluene, dioxane, dichloroethane, methylene chloride, chloroform, in the presence of a base such as pyridine or triethylamine, at a temperature varying between about 0° C. and about 50° C.

The compounds of formula (XII) may be prepared, for example, by reacting a compound of formula (X), as defined above, with a compound of formula (XIII)

wherein $R_4$, $R_{10}$, $R_{11}$ and $R_{13}$ are as defined above, using the same experimental conditions specified above for the reaction between a compound of formula (X) and a compound of formula (XI).

The compounds of formula (IV), (VI), (VII), (VIII), (IX), (X), (XI) and (XIII) are known compounds or may be prepared by conventional methods: in some cases they are commercially available products.

The compounds of this invention possess anti-inflammatory activity as demonstrated e.g. by the fact that they are active, after oral administration, in inhibiting: (A) the oedema formation in the hind paw of rats in response to a subplanter injection of carrageenin, according to the method of C. A. Winter et al. (J. Phar-mac. Exp. Therap. 1963, 141, 369) and P. Lence (Arch. Int. Pharmacodyn., 1962, 136, 237), and (B) the Reversed Passive Arthus Reaction (RPAR) in rat paw, induced by the interaction of antigen and antibody resulting in the formation of precipitating immune complex, followed by fixation of complement and accumulation of polymorphonuclear leucocytes at a focal point (D. K. Gemmell, J. Cottney and A. J. Lewis: Agents and Actions 9/1 pag. 107, 1979).

The compounds of this invention are also endowed with analgesic activity. The analgesic activity was assessed, for example, by means of phenylquinone test in mice according to Siegmund [Siegmund et al. Proc. Soc. Exper. Biol. Med., 95, 729 (1957)].

Therefore the compounds of the invention may be used in therapy to treat pains and inflammatory processes, for example, rheumatoid arthritis and osteoarthrosis.

The following Table I, shows, for example, the approximate $ED_{25}$ values of the antiinflammatory activity in the carrageenin induced oedema test, in the rat after oral administration, for some compounds of this invention:

TABLE I

| Compound | Antiinflammatory activity carrageenin induced oedema |
|---|---|
| 1-phenyl-7-oxo-1H,7H—pyrazolo[1,5-a]pyrimidine-6-N—(2-pyridyl)-carboxamide | $ED_{25}$ = 16 mg/kg |
| 5-methyl-1-phenyl-7-oxo-1H,7H—pyrazolo[1,5-a]pyrimidine-6-N—(2-pyridyl)-carboxamide | $ED_{25}$ = 9.8 mg/kg |

The compounds of formula (I), wherein $R_1$ is $C_1$–$C_6$ alkyl and $R_5$ is hydroxy or $C_1$–$C_6$ alkoxy, are known compounds, e.g., they are described in Published Japan Patent Application No. 14424/66 and in Belgian Patent No. 847,698 and, in fact, they are excluded by the previously reported proviso.

A pharmacological comparison has shown that the compounds of this invention are more active, as anti-inflammatory agents, than those of the above cited prior art.

For example, the compound of this invention 1-methyl-7-oxo-1H,7H-pyrazolo[1,5-a]pyrimidine-6-N-(2-pyridyl)-carboxamide (internal code FCE 23081) was tested versus the compound of the above prior art 1-methyl-7-oxo-1H,7H-pyrazolo[1,5-a]pyrimidine-6-carboxylic acid, ethyl ester (internal code SR 5444/50) according to the carrageenin and RPAR tests described above, and the following results were obtained:

(a) in the carrageenin induced oedema test in the rat, after oral administration at a dosage of 100 mg/kg body weight, the anti-inflammatory activity of the compound FCE 23081 was found to be about three times higher than that of the compound SR 5444/50; and (b) in the RPAR test in the rat, after oral administration at a dosage of 100 mg/kg body weight, the compound SR 5444/50 was found to be totally inactive; on the contrary the compound FCE 23081 was found to strongly inhibit the RPAR reaction.

In view of their high therapeutic index, the compounds of the invention can be used safely in medicine. For example, the approximate acute toxicity ($LD_{50}$) of the compounds 1-phenyl-7-oxo-1H,7H-pyrazolo[1,5-a]pyrimidine-6-N-(2-pyridyl)-carboxamide, 1-phenyl-7-oxo-1H,7H-pyrazolo[1,5-a]pyrimidine-6-carboxylic acid and 5-methyl-1-phenyl-7-oxo-1H,7H-pyrazolo[1,5-a]pyrimidine-6-N-(2-pyridyl)-carboxamide in the mouse, determined by single administration of increasing doses and measured on the seventh day after the treatment, is higher than 800 mg/kg per os. Analogous toxicity data have been found for other compounds of the invention.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 20 to about 200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. The following examples illustrate but do not limit the invention.

EXAMPLE 1

1-phenyl-3-amino-pyrazole, m.p. 90°–91° C. (18 g) was reacted with diethyl ethoxymethylenemalonate (29.3 g) in anhydrous ethanol (180 ml) at the reflux temperature for 15 hours. After cooling the solution was evaporated in vacuo to dryness: the residue was dissolved in isopropyl ether (200 ml) and decolorized by charcoal. Crystallization obtained by dilution with hexane gave diethyl N-(1-phenyl-pyrazol-3-yl)-aminomethylenemalonate, m.p. 81°–82° C. (31 g), which was reacted with polyphosphoric acid (13 g; 6.1 g of $P_2O_5$ and 6.9 g of $H_3PO_4$) and $POCl_3$ (57 g) under stirring at the reflux temperature for 30 minutes. After cooling the reaction mixture was diluted with ice water and then the solution was decolorized, with charcoal: neutralization with 35% NaOH gave a precipitate which was filtered and washed with water. Washing with hexane gave 1-phenyl-7-oxo-1H,7H-pyrazolo[1,5-a]pyrimidine-6-carboxylic acid, ethyl ester, m.p. 187°–190° C. (24.2 g), which was hydrolized by heating with a mixture 1:1 of 37% HCl:acetic acid (1.2 l) at the reflux temperature for 4 hours. After cooling the reaction mixture was neutralized to pH=6 with 35% NaOH and the precipitate was filtered and washed with water: crystallization from isopropyl alcohol gave 9.7 g of 1-phenyl-7-oxo-1H,7H-pyrazolo[1,5-a]pyrimidine-6-carboxylic acid m.p. 185°–190° C. dec., N.M.R. (DMSO-$d_6$) δ p.p.m.: 6.94 (d) (1H, C-3 proton), 7.59 (s) (5H, phenyl protons), 8.74 (d) (1H, C-2 proton), 8.81 (s) (C-5 proton).

By proceeding analogously the following ethyl esters, and after hydrolysis, the following acids were prepared:

2-chloro-1-phenyl-7-oxo-1H,7H-pyrazolo[1,5-a]pyrimidine-6-carboxylic acid, ethyl ester, m.p. 196° C.;

1-(2-methyl-phenyl)-7-oxo-1H,7H-pyrazolo[1,5-a]pyrimidine-6-carboxylic acid, ethyl ester;

1-(3-methyl-phenyl)-7-oxo-1H,7H-pyrazolo[1,5-a]pyrimidine-6-carboxylic acid, ethyl ester;

1-(4-methyl-phenyl)-7-oxo-1H,7H-pyrazolo[1,5-a]pyrimidine-6-carboxylic acid, ethyl ester;

1-(2-methoxy-phenyl)-7-oxo-1H,7H-pyrazolo[1,5-a]pyrimidine-6-carboxylic acid, ethyl ester;

1-(4-methoxy-phenyl)-7-oxo-1H,7H-pyrazolo[1,5-a]pyrimidine-6-carboxylic acid, ethyl ester;

1-(4-nitro-phenyl)-7-oxo-1H,7H-pyrazolo[1,5-a]pyrimidine-6-carboxylic acid, ethyl ester, m.p. 240°–250° C.;

1-(4-fluoro-phenyl)-7-oxo-1H,7H-pyrazolo[1,5-a]pyrimidine-6-carboxylic acid, ethyl ester, m.p. 215°–220° C. dec.;

1-(2-chloro-phenyl)-7-oxo-1H,7H-pyrazolo[1,5-a]pyrimidine-6-carboxylic acid, ethyl ester;

1-(3-chloro-phenyl)-7-oxo-1H,7H-pyrazolo[1,5-a]pyrimidine-6-carboxylic acid, ethyl ester, m.p. 200°–205° C.;

1-(4-chloro-phenyl)-7-oxo-1H,7H-pyrazolo[1,5-a]pyrimidine-6-carboxylic acid, ethyl ester, m.p. 181°–183° C.;

1-(3-trifluoromethyl-phenyl)-7-oxo-1H,7H-pyrazolo[1,5-a]pyrimidine-6-carboxylic acid, ethyl ester, m.p. 181°–183° C.;

3-methyl-1-phenyl-7-oxo-1H,7H-pyrazolo[1,5-a]pyrimidine-6-carboxylic acid, ethyl ester, m.p. 182°–185° C.;

1-(3-chloro-phenyl)-3-methyl-7-oxo-1H,7H-pyrazolo[1,5-a]pyrimidine-6-carboxylic acid, ethyl ester;

1-(4-chloro-phenyl)-3-methyl-7-oxo-1H,7H-pyrazolo[1,5-a]pyrimidine-6-carboxylic acid, ethyl ester;

1-(4-chloro-phenyl)-2-methyl-7-oxo-1H,7H-pyrazolo[1,5-a]pyrimidine-6-carboxylic acid, ethyl ester;

3-methyl-1-(4-methyl-phenyl)-7-oxo-1H,7H-pyrazolo[1,5-a]pyrimidine-6-carboxylic acid, ethyl ester;

2-methyl-1-phenyl-7-oxo-1H,7H-pyrazolo[1,5-a]pyrimidine-6-carboxylic acid, ethyl ester, m.p. 160°–163° C.;

3-bromo-1-phenyl-7-oxo-1H,7H-pyrazolo[1,5-a]pyrimidine-6-carboxylic acid, ethyl ester, m.p. 185°–187° C.;

1-(2-methyl-phenyl)-7-oxo-1H,7H-pyrazolo[1,5-a]pyrimidine-6-carboxylic acid;

1-(3-methyl-phenyl)-7-oxo-1H,7H-pyrazolo[1,5-a]pyrimidine-6-carboxylic acid;

1-(4-methyl-phenyl)-7-oxo-1H,7H-pyrazolo[1,5-a]pyrimidine-6-carboxylic acid, m.p. 185°–188° C. dec.;

1-(2-methoxy-phenyl)-7-oxo-1H,7H-pyrazolo[1,5-a]pyrimidine-6-carboxylic acid;

1-(3-methoxy-phenyl)-7-oxo-1H,7H-pyrazolo[1,5-a]pyrimidine-6-carboxylic acid;

1-(4-methoxy-phenyl)-7-oxo-1H,7H-pyrazolo[1,5-a]pyrimidine-6-carboxylic acid;

1-(4-fluoro-phenyl)-7-oxo-1H,7H-pyrazolo[1,5-a]pyrimidine-6-carboxylic acid;

1-(2-chloro-phenyl)-7-oxo-1H,7H-pyrazolo[1,5-a]pyrimidine-6-carboxylic acid;

1-(3-chloro-phenyl)-7-oxo-1H,7H-pyrazolo[1,5-a]pyrimidine-6-carboxylic acid;

1-(4-chloro-phenyl)-7-oxo-1H,7H-pyrazolo[1,5-a]pyrimidine-6-carboxylic acid;

1-(3-trifluoromethyl-phenyl)-7-oxo-1H,7H-pyrazolo[1,5-a]pyrimidine-6-carboxylic acid;

3-methyl-1-phenyl-7-oxo-1H,7H-pyrazolo[1,5-a]pyrimidine-6-carboxylic acid;

2-chloro-1-phenyl-7-oxo-1H,7H-pyrazolo[1,5-a]pyrimidine-6-carboxylic acid;

3-methyl-1-(4-methyl-phenyl)-7-oxo-1H,7H-pyrazolo[1,5-a]pyrimidine-6-carboxylic acid;

1-(3-chloro-phenyl)-3-methyl-7-oxo-1H,7H-pyrazolo[1,5-a]pyrimidine-6-carboxylic acid;

1-(4-chloro-phenyl)-3-methyl-7-oxo-1H,7H-pyrazolo[1,5-a]pyrimidine-6-carboxylic acid; and 1-(4-methoxy-phenyl)-3-methyl-7-oxo-1H,7H-pyrazolo[1,5-a]pyrimidine-6-carboxylic acid.

EXAMPLE 2

By proceeding according to Example 1, using diethyl (1-ethoxy-alkylidene)-malonates or diethyl (1-ethoxy-benzylidene)-malonate, the following esters, and, after hydrolysis, the following acids were prepared:

5-methyl-1-phenyl-7-oxo-1H,7H-pyrazolo[1,5-a]pyrimidine-6-carboxylic acid, ethyl ester, m.p. 172°–173° C.;

5-methyl-1-(4-methyl-phenyl)-7-oxo-1H,7H-pyrazolo[1,5-a]pyrimidine-6-carboxylic acid, ethyl ester;

1-(3-chloro-phenyl)-5-methyl-7-oxo-1H,7H-pyrazolo[1,5-a]pyrimidine-6-carboxylic acid, ethyl ester;

1-(4-chloro-phenyl)-5-methyl-7-oxo-1H,7H-pyrazolo[1,5-a]pyrimidine-6-carboxylic acid, ethyl ester;

1-(4-fluoro-phenyl)-5-methyl-7-oxo-1H,7H-pyrazolo[1,5-a]pyrimidine-6-carboxylic acid, ethyl ester, m.p. 175°–177° C.;

1,5-diphenyl-7-oxo-1H,7H-pyrazolo[1,5-a]pyrimidine-6-carboxylic acid, ethyl ester;

5-ethyl-1-phenyl-7-oxo-1H,7H-pyrazolo[1,5-a]pyrimidine-6-carboxylic acid;

5-ethyl-1-phenyl-7-oxo-1H,7H-pyrazolo[1,5-a]pyrimidine-6-carboxylic acid, ethyl ester, m.p. 119°–120° C.;

5-methyl-1-phenyl-7-oxo-1H,7H-pyrazolo[1,5-a]pyrimidine-6-carboxylic acid;

5-methyl-1-(4-methyl-phenyl)-7-oxo-1H,7H-pyrazolo[1,5-a]pyrimidine-6-carboxylic acid;

1-(3-chloro-phenyl)-5-methyl-7-oxo-1H,7H-pyrazolo[1,5-a]pyrimidine-6-carboxylic acid;

1-(4-chloro-phenyl)-5-methyl-7-oxo-1H,7H-pyrazolo[1,5-a]pyrimidine-6-carboxylic acid;

1-(4-fluoro-phenyl)-5-methyl-7-oxo-1H,7H-pyrazolo[1,5-a]pyrimidine-6-carboxylic acid; and 1,5-diphenyl-7-oxo-1H,7H-pyrazolo[1,5-a]pyrimidine-6-carboxylic acid.

EXAMPLE 3

By proceeding according to Examples 1 and 2, starting from suitable 1-pyridyl-3-amino-pyrazoles, the following esters, and, after hydrolysis, the following acids were prepared:

1-(2-pyridyl)-7-oxo-1H,7H-pyrazolo[1,5-a]pyrimidine-6-carboxylic acid, ethyl ester, m.p. 138°–139° C.;

1-(3-pyridyl)-7-oxo-1H,7H-pyrazolo[1,5-a]pyrimidine-6-carboxylic acid, ethyl ester, m.p. 203°–207° C.;

1-(4-pyridyl)-7-oxo-1H,7H-pyrazolo[1,5-a]pyrimidine-6-carboxylic acid, ethyl ester;

5-methyl-1-(2-pyridyl)-7-oxo-1H,7H-pyrazolo[1,5-a]pyrimidine-6-carboxylic acid, ethyl ester, m.p. 103°–104° C.;

5-methyl-1-(3-pyridyl)-7-oxo-1H,7H-pyrazolo[1,5-a]pyrimidine-6-carboxylic acid, ethyl ester;

1-(2-pyridyl)-7-oxo-1H,7H-pyrazolo[1,5-a]pyrimidine-6-carboxylic acid;

1-(3-pyridyl)-7-oxo-1H,7H-pyrazolo[1,5-a]pyrimidine-6-carboxylic acid;

1-(4-pyridyl)-7-oxo-1H,7H-pyrazolo[1,5-a]pyrimidine-6-carboxylic acid;

5-methyl-1-(2-pyridyl)-7-oxo-1H,7H-pyrazolo[1,5-a]pyrimidine-6-carboxylic acid; and 5-methyl-1-(3-pyridyl)-7-oxo-1H,7H-pyrazolo[1,5-a]pyrimidine-6-carboxylic acid.

EXAMPLE 4

1-benzyl-3-amino-pyrazole, m.p. 57°–59° C. (4 g) was reacted with diethyl ethoxymethylenemalonate (6 g) in anhydrous ethanol (40 ml) at the reflux temperature for 3 hours. After cooling the solution was evaporated in vacuo to dryness. Crystallization obtained by dilution with hexane gave diethyl N-(1-benzyl-pyrazol-3-yl)-aminomethylenemalonate, m.p. 60°–62° C. (7.5 g), which was reacted with polyphosphoric acid (3.2 g: 1.5 g of $P_2O_5$ and 1.7 g of $H_3PO_4$) and $POCl_3$ (13.5 g) under stirring at 120° C. for 30 minutes. After cooling the reaction mixture was diluted with ice water: neutralization with 35% NaOH gave a precipitate which was filtered and washed with water. Crystallization from methanol gave 6 g of 1-benzyl-7-oxo-1H,7H-pyrazolo[1,5-a]pyrimidine-6-carboxylic acid, ethyl ester, m.p. 172°–173° C., which was hydrolized by heating with a mixture 1:1 of 37% HCl:acetic acid (300 ml) at the reflux temperature for 4 hours. After cooling the reaction mixture was neutralized to pH=6 with 35% NaOH and the precipitate was filtered and washed with water: crystallization from isopropyl alcohol gave 9.7 g of 1-benzyl-7-oxo-1H,7H-pyrazolo[1,5-a]pyrimidine-6-carboxylic acid, m.p. 198°–199° C.

By proceeding analogously, using suitable diethyl (1-ethoxy-alkylidene)-malonates, the following esters and, after hydrolysis, the following acids were prepared:

1-benzyl-5-methyl-7-oxo-1H,7H-pyrazolo[1,5-a]pyrimidine-6-carboxylic acid, ethyl ester;
1-benzyl-5-ethyl-7-oxo-1H,7H-pyrazolo[1,5-a]pyrimidine-6-carboxylic acid, ethyl ester;
1-benzyl-5-phenyl-7-oxo-1H,7H-pyrazolo[1,5-a]pyrimidine-6-carboxylic acid, ethyl ester;
1-benzyl-5-methyl-7-oxo-1H,7H-pyrazolo[1,5-a]pyrimidine-6-carboxylic acid;
1-benzyl-5-ethyl-7-oxo-1H,7H-pyrazolo[1,5-a]pyrimidine-6-carboxylic acid; and
1-benzyl-5-phenyl-7-oxo-1H,7H-pyrazolo[1,5-a]pyrimidine-6-carboxylic acid.

EXAMPLE 5

1-phenyl-7-oxo-1H,7H-pyrazolo[1,5-a]pyrimidine-6-carboxylic acid (3 g), was reacted with thionyl chloride (2.8 g) in dioxane (70 ml) at the reflux temperature for 1 hour, then the mixture was evaporated in vacuo to dryness. The crude 6-chlorocarbonyl-1-phenyl-7-oxo-1H,7H-pyrazolo[1,5-a]pyrimidine was suspended in dioxane (60 ml) and reacted under stirring at room temperature for 30 minutes with methylamine (3.75 g). The precipitate was filtered and washed with water until neutral: crystallization from isopropyl alcohol gave 1.7 g of 1-phenyl-7-oxo-1H,7H-pyrazolo[1,5-a]pyrimidine-6-N-methyl-carboxamide, m.p. 244°–246° C., N.M.R. (CDCl$_3$) δ p.p.m.: 2.92 (d) (3H, —CH$_3$), 6.73 (d) (1H, C-3 proton), 7.37–7.75 (m) (5H, phenyl protons), 7.91 (d) (1H, C-2 proton), 8.70 (bs) (1H, —NHCH$_3$), 9.10 (s) (1H, C-5 proton).

By proceeding analogously, using ammonia or suitable amines, the following compound were prepared:

1-phenyl-7-oxo-1H,7H-pyrazolo[1,5-a]pyrimidine-6-carboxamide, m.p. 265°–270° C. dec.;
1-phenyl-7-oxo-1H,7H-pyrazolo[1,5-a]pyrimidine-6-N-ethyl-carboxamide, m.p. 225°–230° C. dec.;
1-phenyl-7-oxo-1H,7H-pyrazolo[1,5-a]pyrimidine-6-N,N-diethyl-carboxamide, m.p. 146°–147° C.;
1-(2-pyridyl)-7-oxo-1H,7H-pyrazolo[1,5-a]pyrimidine-6-N-ethyl-carboxamide;
1-phenyl-7-oxo-1H,7H-pyrazolo[1,5-a]pyrimidine-6-N-isopropyl-carboxamide, m.p. 220°–225° C. dec.;
5-methyl-1-phenyl-7-oxo-1H,7H-pyrazolo[1,5-a]pyrimidine-6-N-phenyl-carboxamide;
3-methyl-1-phenyl-7-oxo-1H,7H-pyrazolo[1,5-a]pyrimidine-6-N-phenyl-carboxamide;
2-chloro-1-phenyl-7-oxo-1H,7H-pyrazolo[1,5-a]pyrimidine-6-N-phenyl-carboxamide;
1-phenyl-7-oxo-1H,7H-pyrazolo[1,5-a]pyrimidine-6-N-phenyl-carboxamide, m.p. 245°–247° C.;
1-phenyl-7-oxo-1H,7H-pyrazolo[1,5-a]pyrimidine-6-N-(3-pyridyl)-carboxamide, m.p. 207°–210° C.;
1-phenyl-7-oxo-1H,7H-pyrazolo[1,5-a]pyrimidine-6-N-(4-methyl-phenyl)-carboxamide;
1-(3-chloro-phenyl)-7-oxo-1H,7H-pyrazolo[1,5-a]pyrimidine-6-N-methyl-carboxamide;
1-(4-chloro-phenyl)-7-oxo-1H,7H-pyrazolo[1,5-a]pyrimidine-6-N-methyl-carboxamide;
1-(4-chloro-phenyl)-7-oxo-1H,7H-pyrazolo[1,5-a]pyrimidine-6-N-ethyl-carboxamide;
1-(4-chloro-phenyl)-7-oxo-1H,7H-pyrazolo[1,5-a]pyrimidine-6-N-isopropyl-carboxamide;
1-(4-pyridyl)-7-oxo-1H,7H-pyrazolo[1,5-a]pyrimidine-6-N-methyl-carboxamide;
1-(2-pyridyl)-7-oxo-1H,7H-pyrazolo[1,5-a]pyrimidine-6-N-methyl-carboxamide;
1-(3-pyridyl)-7-oxo-1H,7H-pyrazolo[1,5-a]pyrimidine-6-N-methyl-carboxamide;
1-(3-chloro-phenyl)-7-oxo-1H,7H-pyrazolo[1,5-a]pyrimidine-6N-phenyl-carboxamide;
1-(4-chloro-phenyl)-7-oxo-1H,7H-pyrazolo[1,5-a]pyrimidine-6-N-phenyl-carboxamide;
1-phenyl-7-oxo-1H,7H-pyrazolo[1,5-a]pyrimidine-6-N-(4-chloro-phenyl)-carboxamide;
1-phenyl-7-oxo-1H,7H-pyrazolo[1,5-a]pyrimidine-6-N-(6-methoxy-3-pyridyl)-carboxamide;
1-(3-pyridyl)-7-oxo-1H,7H-pyrazolo[1,5-a]pyrimidine-6-N-ethyl-carboxamide;
5-methyl-1-phenyl-7-oxo-1H,7H-pyrazolo[1,5-a]pyrimidine-6-N-methyl-carboxamide;
5-methyl-1-phenyl-7-oxo-1H,7H-pyrazolo[1,5-a]pyrimidine-6-N-ethyl-carboxamide;
5-methyl-1-phenyl-7-oxo-1H,7H-pyrazolo[1,5-a]pyrimidine-6-N,N-diethyl-carboxamide;
5-methyl-1-phenyl-7-oxo-1H,7H-pyrazolo[1,5-a]pyrimidine-6-N-isopropyl-carboxamide;
5-methyl-1-phenyl-7-oxo-1H,7H-pyrazolo[1,5-a]pyrimidine-6-N-(4-chloro-phenyl)-carboxamide;
5-methyl-1-phenyl-7-oxo-1H,7H-pyrazolo[1,5-a]pyrimidine-6-N-(4-methoxy-phenyl)-carboxamide; and
1-(4-pyridyl)-7-oxo-1H,7H-pyrazolo[1,5-a]pyrimidine-6-N-ethyl-carboxamide.

EXAMPLE 6

By proceeding according to Example 5, using suitable amines, the following compounds were prepared:

1-benzyl-7-oxo-1H,7H-pyrazolo[1,5-a]pyrimidine-6-N,N-diethyl-carboxamide;
1-benzyl-7-oxo-1H,7H-pyrazolo[1,5-a]pyrimidine-6-N-ethyl-carboxamide;
1-benzyl-7-oxo-1H,7H-pyrazolo[1,5-a]pyrimidine-6-N-isopropyl-carboxamide;
1-benzyl-7-oxo-1H,7H-pyrazolo[1,5-a]pyrimidine-6-N-(4-methyl-phenyl)-carboxamide;
1-benzyl-7-oxo-1H,7H-pyrazolo[1,5-a]pyrimidine-6-N-(4-chloro-phenyl)-carboxamide;
1-benzyl-5-methyl-7-oxo-1H,7H-pyrazolo[1,5-a]pyrimidine-6-N-methyl-carboxamide;
1-benzyl-5-methyl-7-oxo-1H,7H-pyrazolo[1,5-a]pyrimidine-6-N-ethyl-carboxamide;
1-benzyl-5-methyl-7-oxo-1H,7H-pyrazolo[1,5-a]pyrimidine-6-N,N-diethyl-carboxamide;
1-benzyl-5-methyl-7-oxo-1H,7H-pyrazolo[1,5-a]pyrimidine-6-N-isopropyl-carboxamide;
1-benzyl-5-methyl-7-oxo-1H,7H-pyrazolo[1,5-a]pyrimidine-6-N-(4-chloro-phenyl)-carboxamide;
1-benzyl-5-methyl-7-oxo-1H,7H-pyrazolo[1,5-a]pyrimidine-6-N-(4-methoxy-phenyl)-carboxamide;
1-methyl-7-oxo-1H,7H-pyrazolo[1,5-a]pyrimidine-6-N-isopropyl-carboxamide;
1-methyl-7-oxo-1H,7H-pyrazolo[1,5-a]pyrimidine-6-N,N-diethyl-carboxamide;
1,5-dimethyl-7-oxo-1H,7H-pyrazolo[1,5-a]pyrimidine-6-N-methyl-carboxamide;
1-methyl-7-oxo-1H,7H-pyrazolo[1,5-a]pyrimidine-6-N-methyl-carboxamide;

1-methyl-7-oxo-1H,7H-pyrazolo[1,5-a]pyrimidine-6-N-ethyl-carboxamide;
1-methyl-7-oxo-1H,7H-pyrazolo[1,5-a]pyrimidine-6-N-(4-chloro-phenyl)-carboxamide;
1-methyl-7-oxo-1H,7H-pyrazolo[1,5-a]pyrimidine-6-N-(4-methoxy-phenyl)-carboxamide;
1,5-dimethyl-7-oxo-1H,7H-pyrazolo[1,5-a]pyrimidine-6-N-isopropyl-carboxamide;
1-ethyl-5-methyl-7-oxo-1H,7H-pyrazolo[1,5-a]pyrimidine-6-N-methyl-carboxamide;
1-ethyl-7-oxo-1H,7H-pyrazolo[1,5-a]pyrimidine-6-N-isopropyl-carboxamide;
1-ethyl-7-oxo-1H,7H-pyrazolo[1,5-a]pyrimidine-6-N-ethyl-carboxamide;
1,5-dimethyl-7-oxo-1H,7H-pyrazolo[1,5-a]pyrimidine-6-N-ethyl-carboxamide;
1,5-dimethyl-7-oxo-1H,7H-pyrazolo[1,5-a]pyrimidine-6-N,N-diethyl-carboxamide;
1-ethyl-5-methyl-7-oxo-1H,7H-pyrazolo[1,5-a]pyrimidine-6-N-ethyl-carboxamide;
1-ethyl-5-methyl-7-oxo-1H,7H-pyrazolo[1,5-a]pyrimidine-6-N-isopropyl-carboxamide;
1,5-dimethyl-7-oxo-1H,7H-pyrazolo[1,5-a]pyrimidine-6-N-(4-chloro-phenyl)-carboxamide;
1,5-dimethyl-7-oxo-1H,7H-pyrazolo[1,5-a]pyrimidine-6-N-(4-methoxy-phenyl)-carboxamide;
1-(2-pyridyl)-7-oxo-1H,7H-pyrazolo[1,5-a]pyrimidine-6-N-isopropyl-carboxamide;
1-(3-pyridyl)-7-oxo-1H,7H-pyrazolo[1,5-a]pyrimidine-6-N-isopropyl-carboxamide;
1-(4-pyridyl)-7-oxo-1H,7H-pyrazolo[1,5-a]pyrimidine-6-N-isopropyl-carboxamide;
5-methyl-1-(2-pyridyl)-7-oxo-1H,7H-pyrazolo[1,5-a]pyrimidine-6-N-methyl-carboxamide;
5-methyl-1-(3-pyridyl)-7-oxo-1H,7H-pyrazolo[1,5-a]pyrimidine-6-N-methyl-carboxamide;
5-methyl-1-(4-pyridyl)-7-oxo-1H,7H-pyrazolo[1,5-a]pyrimidine-6-N-methyl-carboxamide;
5-methyl-1-(2-pyridyl)-7-oxo-1H,7H-pyrazolo[1,5-a]pyrimidine-6-N-ethyl-carboxamide;
5-methyl-1-(3-pyridyl)-7-oxo-1H,7H-pyrazolo[1,5-a]pyrimidine-6-N-ethyl-carboxamide;
5-methyl-1-(4-pyridyl)-7-oxo-1H,7H-pyrazolo[1,5-a]pyrimidine-6-N-ethyl-carboxamide;
5-methyl-1-(2-pyridyl)-7-oxo-1H,7H-pyrazolo[1,5-a]pyrimidine-6-N-isopropyl-carboxamide;
5-methyl-1-(3-pyridyl)-7-oxo-1H,7H-pyrazolo[1,5-a]pyrimidine-6-N-isopropyl-carboxamide; and
5-methyl-1-(4-pyridyl)-7-oxo-1H,7H-pyrazolo[1,5-a]pyrimidine-6-N-isopropyl-carboxamide.

EXAMPLE 7

1-phenyl-7-oxo-1H,7H-pyrazolo[1,5-a]pyrimidine-6-carboxylic acid (1.2 g) was reacted with thionyl chloride (0.8 ml) in dioxane (30 ml) at the reflux temperature for 3 hours, then the mixture was evaporated in vacuo to dryness. The residue was dissolved in dioxane (30 ml) and reacted with 2-(diethylamino)-ethanol (1.2 g) at room temperature for 24 hours. After dilution with water and alkalinization with $Na_2CO_3$ the precipitate was extracted with ethyl acetate: evaporation to dryness and crystallization from chloroformethanol gave 0.7 g of 1-phenyl-7-oxo-1H,7H-pyrazolo[1,5-a]pyrimidine-6-carboxylic acid, 2-(diethylamino)-ethyl ester, m.p. 127°–130° C.

By proceeding analogously the following compounds were prepared:

1-(4-fluoro-phenyl)-7-oxo-1H,7H-pyrazolo[1,5-a]pyrimidine-6-carboxylic acid, 2-(diethylamino)-ethyl ester;
1-(4-chloro-phenyl)-7-oxo-1H,7H-pyrazolo[1,5-a]pyrimidine-6-carboxylic acid, 2-(diethylamino)-ethyl ester;
1-(3-chloro-phenyl)-7-oxo-1H,7H-pyrazolo[1,5-a]pyrimidine-6-carboxylic acid, 2-(diethylamino)-ethyl ester;
1-phenyl-7-oxo-1H,7H-pyrazolo[1,5-a]pyrimidine-6-carboxylic acid, 2-(diethylamino)-ethyl ester, m.p. 153°–154° C.;
1-(4-methyl-phenyl)-7-oxo-1H,7H-pyrazolo[1,5-a]pyrimidine-6-carboxylic acid, 2-(diethylamino)-ethyl ester;
1-(2-pyridyl)-7-oxo-1H,7H-pyrazolo[1,5-a]pyrimidine-6-carboxylic acid, 2-(diethylamino)-ethyl ester;
1-(3-pyridyl)-7-oxo-1H,7H-pyrazolo[1,5-a]pyrimidine-6-carboxylic acid, 2-(diethylamino)-ethyl ester;
5-methyl-1-phenyl-7-oxo-1H,7H-pyrazolo[1,5-a]pyrimidine-6-carboxylic acid, 2-(diethylamino)-ethyl ester;
3-methyl-1-phenyl-7-oxo-1H,7H-pyrazolo[1,5-a]pyrimidine-6-carboxylic acid, 2-(diethylamino)-ethyl ester; and
1-benzyl-7-oxo-1H,7H-pyrazolo[1,5-a]pyrimidine-6-carboxylic acid, 2-(diethylamino)-ethyl ester.

EXAMPLE 8

6-chlorocarbonyl-1-phenyl-7-oxo-1H,7H-pyrazolo[1,5-a]pyrimidine (2.7 g) was reacted with N-(2-amino-ethyl)-piperidine (2.5 g) in dioxane (55 ml) at room temperature for 30 minutes. After evaporation in vacuo to dryness, the reaction product was dissolved in chloroform and then purified over a $SiO_2$ column using $CHCl_3:CH_3OH=85:15$ as eluent. Crystallization from $CH_2Cl_2$-isopropyl ether gave 2.1 g of 1-phenyl-7-oxo-1H,7H-pyrazolo[1,5-a]pyrimidine-6-N-(2-piperidino-ethyl)-carboxamide, m.p. 136°–138° C.

By proceeding analogously the following compounds were prepared:
1-phenyl-7-oxo-1H,7H-pyrazolo[1,5-a]pyrimidine-6-N-(2-morpholino-ethyl)-carboxamide, m.p. 179°–180° C.;
1-phenyl-7-oxo-1H,7H-pyrazolo[1,5-a]pyrimidine-6-N-[2-(pyrrolidin-1-yl)-ethyl]-carboxamide, m.p. 145°–148° C.;
1-phenyl-7-oxo-1H,7H-pyrazolo[1,5-a]pyrimidine-6-N-[2-(N,N-diethylamino)-ethyl]-carboxamide, m.p. 135°–137° C.;
1-benzyl-7-oxo-1H,7H-pyrazolo[1,5-a]pyrimidine-6-N-(2-piperidino-ethyl)-carboxamide;
1-benzyl-7-oxo-1H,7H-pyrazolo[1,5-a]pyrimidine-6-N-[2-(N,N-diethylamino)-ethyl]-carboxamide;
1-methyl-7-oxo-1H,7H-pyrazolo[1,5-a]pyrimidine-6-N-(2-piperidino-ethyl)-carboxamide;
1-methyl-7-oxo-1H,7H-pyrazolo[1,5-a]pyrimidine-6-N-[2-(N,N-diethylamino)-ethyl]-carboxamide;
1-(2-pyridyl)-7-oxo-1H,7H-pyrazolo[1,5-a]pyrimidine-6-N-(2-piperidino-ethyl)-carboxamide;
1-(2-pyridyl)-7-oxo-1H,7H-pyrazolo[1,5-a]pyrimidine-6-N-[2-(N,N-diethylamino)-ethyl]-carboxamide;
1-(3-pyridyl)-7-oxo-1H,7H-pyrazolo[1,5-a]pyrimidine-6-N-(2-piperidino-ethyl)-carboxamide;
1-(2-pyridyl)-7-oxo-1H,7H-pyrazolo[1,5-a]pyrimidine-6-N-(2-morpholino-ethyl)-carboxamide;
1-(3-pyridyl)-7-oxo-1H,7H-pyrazolo[1,5-a]pyrimidine-6-N-[2-(N,N-diethylamino)-ethyl]-carboxamide;

5-methyl-1-phenyl-7-oxo-1H-7H-pyrazolo[1,5-a]pyrimidine-6-N-(2-piperidino-ethyl)-carboxamide;

5-methyl-1-(3-pyridyl)-7-oxo-1H,7H-pyrazolo[1,5-a]pyrimidine-6-N-(2-piperidino-ethyl)-carboxamide; and 5-methyl-1-(2-pyridyl)-7-oxo-1H,7H-pyrazolo[1,5-a]pyrimidine-6-N-(2-piperidino-ethyl)-carboxamide.

EXAMPLE 9

6-chlorocarbonyl-1-phenyl-7-oxo-1H,7H-pyrazolo[1,5-a]pyrimidine (2.7 g), prepared according to Example 5, was reacted with piperidine (1.65 g) in dioxane (45 ml) at room temperature for 30 minutes. After evaporation in vacuo to dryness, the reaction product was dissolved in chloroform and then purified over a $SiO_2$ column using chloroform:methanol=95:5 as eluent.

Crystallization from $CH_2Cl_2$-isopropyl ether gave 2.35 g of 1-phenyl-6-piperidinocarbonyl-1H,7H-pyrazolo[1,5-a]pyrimidine-7-one, m.p. 160°–161° C.

By proceeding analogously the following compounds were prepared:

6-(4-methyl-piperazin-1-yl)carbonyl-1-phenyl-1H,7H-pyrazolo[1,5-a]pyrimidine-7-one, m.p. 185°–186° C.;

6-morpholinocarbonyl-1-phenyl-1H,7H-pyrazolo[1,5-a]pyrimidine-7-one, m.p. 150°–152° C.;

6-morpholinocarbonyl-1-(3-pyridyl)-1H,7H-pyrazolo[1,5-a]pyrimidine-7-one;

6-(4-methyl-piperazin-1-yl)carbonyl-1-(3-pyridyl)-1H,7H-pyrazolo[1,5-a]pyrimidine-7-one;

6-piperidinocarbonyl-1-(3-pyridyl)-1H,7H-pyrazolo[1,5-a]pyrimidine-7-one;

5-methyl-6-(4-methyl-piperazin-1-yl)carbonyl-1-phenyl-1H,7H-pyrazolo[1,5-a]pyrimidine-7-one;

6-piperidinocarbonyl-1-(2-pyridyl)-1H,7H-pyrazolo[1,5-a]pyrimidine-7-one;

5-methyl-6-morpholinocarbonyl-1-phenyl-1H,7H-pyrazolo[1,5-a]pyrimidine-7-one;

5-methyl-6-morpholinocarbonyl-1-(3-pyridyl)-1H,7H-pyrazolo[1,5-a]pyrimidine-7-one;

5-methyl-6-(4-methyl-piperazin-1-yl)carbonyl-1-(3-pyridyl)-1H,7H-pyrazolo[1,5-a]pyrimidine-7-one;

5-methyl-6-piperidinocarbonyl-1-(3-pyridyl)-1H,7H-pyrazolo[1,5-a]pyrimidine-7-one;

1-benzyl-6-morpholinocarbonyl-1H,7H-pyrazolo[1,5-a]pyrimidine-7-one;

1-benzyl-6-(4-methyl-piperazin-1-yl)carbonyl-1H,7H-pyrazolo[1,5-a]pyrimidine-7-one;

1-methyl-6-morpholinocarbonyl-1H,7H-pyrazolo[1,5-a]pyrimidine-7-one;

1-methyl-6-(4-methyl-piperazin-1-yl)carbonyl-1H,7H-pyrazolo[1,5-a]pyrimidine-7-one;

6-morpholinocarbonyl-1-(2-pyridyl)-1H,7H-pyrazolo[1,5-a]pyrimidine-7-one;

6-(4-methyl-piperazin-1-yl)carbonyl-1-(2-pyridyl)-1H,7H-pyrazolo[1,5-a]pyrimidine-7-one;

5-methyl-6-piperidinocarbonyl-1-(2-pyridyl)-1H,7H-pyrazolo[1,5-a]pyrimidine-7-one;

5-methyl-6-morpholinocarbonyl-1-(2-pyridyl)-1H,7H-pyrazolo[1,5-a]pyrimidine-7-one; and 5-methyl-6-(4-methyl-piperazin-1-yl)-1-(2-pyridyl)-1H,7H-pyrazolo[1,5-a]pyrimidine-7-one.

EXAMPLE 10

1-phenyl-7-oxo-1H,7H-pyrazolo[1,5-a]pyrimidine-6-carboxylic acid (5.1 g) was reacted with 2-aminothiazole (4 g) in polyphosphoric acid (90 g: 47.7 g of $H_3PO_4$ and 42.3 g of $P_2O_5$) under stirring at 120° C. for 20 hours. After cooling, dilution with ice water and neutralization with 35% NaOH, the precipitate was filtered and washed with water: crystallization from $CHCl_3$-methanol gave 4.5 g of 1-phenyl-7-oxo-1H,7H-pyrazolo[1,5-a]pyrimidine-6-N-(2-thiazolyl)-carboxamide, m.p. 245°–247° C. dec., N.M.R. ($CDCl_3$) δ p.p.m.: 6.72 (d) (1H, C-3 proton), 6.84 (d) (1H, C-5 thiazolyl proton), 7.4–7.7 (m) (6H, phenyl protons and C-4 thiazolyl proton), 7.98 (d) (1H, C-2 proton), 9.45 (s) (1H, C-5 proton), >11 (bs) (1H, —CONH—).

By proceeding analogously the following compounds were prepared:

3-methyl-1-phenyl-7-oxo-1H,7H-pyrazolo[1,5-a]pyrimidine-6-N-(2-thiazolyl)-carboxamide;

5-methyl-1-phenyl-7-oxo-1H,7H-pyrazolo[1,5-a]pyrimidine-6-N-(2-thiazolyl)-carboxamide;

1-phenyl-7-oxo-1H,7H-pyrazolo[1,5-a]pyrimidine-6-N-(2-pyridyl)-carboxamide, m.p. 207°–210° C. dec.;

5-ethyl-1-phenyl-7-oxo-1H,7H-pyrazolo[1,5-a]pyrimidine-6-N-(2-thiazolyl)-carboxamide; and 5-methyl-1-phenyl-7-oxo-1H,7H-pyrazolo[1,5-a]pyrimidine-6-N-(2-pyridyl)-carboxamide, m.p. 184°–187° C.

EXAMPLE 11

5-methyl-1-phenyl-7-oxo-1H,7H-pyrazolo[1,5-a]pyrimidine-6-carboxylic acid, ethyl ester (17 g) was reacted with 2-amino-pyridine (10.8 g) in polyphosphoric acid (270 g) under stirring at 120° C. for 2 hours. After cooling, dilution with ice water and neutralization with 35% NaOH, the precipitate was filtered and washed with water: crystallization from $CH_2Cl_2$-methanol gave 14 g of 5-methyl-1-phenyl-7-oxo-1H,7H-pyrazolo[1,5-a]pyrimidine-6-N-(2-pyridyl)-carboxamide, m.p. 186°–187° C., N.M.R. ($CDCl_3$) δ p.p.m.: 2.88 (s) (3H, —$CH_3$), 6.62 (d) (1H, C-3 proton), 6.99 (m) (1H, C-5 pyridyl proton), 7.38–7.50 (m) (5H, phenyl protons), 7.70 (ddd) (1H, C-4 pyridyl proton), 7.82 (d) (1H, C-2 proton), 8.26 (dd) (1H, C-3 pyridyl proton), 8.34 (d) (1H, C-6 pyridyl proton), >10.5 (bs) (1H, —CONH—).

By proceeding analogously the following compounds were prepared:

1-phenyl-7-oxo-1H,7H-pyrazolo[1,5-a]pyrimidine-6-N-(2-pyridyl)-carboxamide, m.p. 207°–210° C.;

1-phenyl-7-oxo-1H,7H-pyrazolo[1,5-a]pyrimidine-6-N-(5-chloro-2-pyridyl)-carboxamide, m.p. 260° C. dec.;

1-phenyl-7-oxo-1H,7H-pyrazolo[1,5-a]pyrimidine-6-N-(5-methyl-2-pyridyl)-carboxamide, m.p. 268°–270° C.;

1-phenyl-7-oxo-1H,7H-pyrazolo[1,5-a]pyrimidine-6-N-(4-methyl-2-pyridyl)-carboxamide, m.p. 210°–215° C. dec.;

1-phenyl-7-oxo-1H,7H-pyrazolo[1,5-a]pyrimidine-6-N-pyrazinyl-carboxamide;

1-phenyl-7-oxo-1H,7H-pyrazolo[1,5-a]pyrimidine-6-N-(6-methyl-2-pyridyl)-carboxamide, m.p. 235°–240° C. dec.;

1-phenyl-7-oxo-1H,7H-pyrazolo[1,5-a]pyrimidine-6-N-(5-bromo-2-pyridyl)-carboxamide;

1-phenyl-7-oxo-1H,7H-pyrazolo[1,5-a]pyrimidine-6-N-(6-hydroxy-2-pyridyl)-carboxamide, m.p. 280°–290° C. dec.;

1-phenyl-7-oxo-1H,7H-pyrazolo[1,5-a]pyrimidine-6-N-(3-methyl-2-pyridyl)-carboxamide, m.p. 252°–254° C.;

1-phenyl-7-oxo-1H,7H-pyrazolo[1,5-a]pyrimidine-6-N-(6-methoxy-2-benzothiazolyl)-carboxamide;

1-phenyl-7-oxo-1H,7H-pyrazolo[1,5-a]pyrimidine-6-N-(4,5-dimethyl-2-thiazolyl)-carboxamide;

1-phenyl-7-oxo-1H,7H-pyrazolo[1,5-a]pyrimidine-6-N-(4-methyl-2-thiazolyl)-carboxamide;
1-phenyl-7-oxo-1H,7H-pyrazolo[1,5-a]pyrimidine-6-N-(2-benzothiazolyl)-carboxamide, m.p. 245°–250° C.;
1-phenyl-7-oxo-1H,7H-pyrazolo[1,5-a]pyrimidine-6-N-(4-phenyl-2-thiazolyl)-carboxamide;
1-phenyl-7-oxo-1H,7H-pyrazolo[1,5-a]pyrimidine-6-N-(1-methyl-3-pyrazolyl)-carboxamide;
1-phenyl-7-oxo-1H,7H-pyrazolo[1,5-a]pyrimidine-6-N-(1-phenyl-3-pyrazolyl)-carboxamide, m.p. 248°–252° C.;
1-phenyl-7-oxo-1H,7H-pyrazolo[1,5-a]pyrimidine-6-N-(5-chloro-2-thiazolyl)-carboxamide;
1-(4-methoxy-phenyl)-7-oxo-1H,7H-pyrazolo[1,5-a]pyrimidine-6-N-(2-pyridyl)-carboxamide;
1-(4-methoxy-phenyl)-7-oxo-1H,7H-pyrazolo[1,5-a]pyrimidine-6-N-(6-methyl-2-pyridyl)-carboxamide;
1-phenyl-7-oxo-1H,7H-pyrazolo[1,5-a]pyrimidine-6-N-(2-pyrimidinyl)-carboxamide, m.p. 200°–205° C. dec.;
1-phenyl-7-oxo-1H,7H-pyrazolo[1,5-a]pyrimidine-6-N-(3,5-dichloro-2-pyridyl)-carboxamide, m.p. 305°–310° C. dec.;
1-phenyl-7-oxo-1H,7H-pyrazolo[1,5-a]pyrimidine-6-N-(4-pyridyl)-carboxamide, m.p. 270°–275° C. dec.;
2-methyl-1-phenyl-7-oxo-1H,7H-pyrazolo[1,5-a]pyrimidine-6-N-(2-pyridyl)-carboxamide, m.p. 225°–230° C. dec.;
1-(4-methoxy-phenyl)-7-oxo-1H,7H-pyrazolo[1,5-a]pyrimidine-6-N-(5-chloro-2-pyridyl)-carboxamide;
1-(4-methoxy-phenyl)-7-oxo-1H,7H-pyrazolo[1,5-a]pyrimidine-6-N-(4,5-dimethyl-2-thiazolyl)-carboxamide;
1-(4-methyl-phenyl)-7-oxo-1H,7H-pyrazolo[1,5-a]pyrimidine-6-N-(5-chloro-2-pyridyl)-carboxamide;
1-(4-methyl-phenyl)-7-oxo-1H,7H-pyrazolo[1,5-a]pyrimidine-6-N-(4,5-dimethyl-2-thiazolyl)-carboxamide;
1-(4-methyl-phenyl)-7-oxo-1H,7H-pyrazolo[1,5-a]pyrimidine-6-N-(2-pyridyl)-carboxamide, m.p. 209°–213° C. dec.;
1-(4-methyl-phenyl)-7-oxo-1H,7H-pyrazolo[1,5-a]pyrimidine-6-N-(6-methyl-2-pyridyl)-carboxamide;
1-(4-methyl-phenyl)-7-oxo-1H,7H-pyrazolo[1,5-a]pyrimidine-6-N-(2-thiazolyl)-carboxamide;
1-(4-methyl-phenyl)-7-oxo-1H,7H-pyrazolo[1,5-a]pyrimidine-6-N-(2-benzothiazolyl)-carboxamide;
1-(4-methyl-phenyl)-7-oxo-1H,7H-pyrazolo[1,5-a]pyrimidine-6-N-(4-methyl-2-thiazolyl)-carboxamide;
1-(4-methyl-phenyl)-7-oxo-1H,7H-pyrazolo[1,5-a]pyrimidine-6-N-(5-chloro-2-thiazolyl)-carboxamide;
1-(4-chloro-phenyl)-7-oxo-1H,7H-pyrazolo[1,5-a]pyrimidine-6-N-(2-pyridyl)-carboxamide, m.p. 254°–257° C.;
1-(4-chloro-phenyl)-7-oxo-1H,7H-pyrazolo[1,5-a]pyrimidine-6-N-(6-methyl-2-pyridyl)-carboxamide;
1-(4-chloro-phenyl)-7-oxo-1H,7H-pyrazolo[1,5-a]pyrimidine-6-N-(2-thiazolyl)-carboxamide;
1-(4-chloro-phenyl)-7-oxo-1H,7H-pyrazolo[1,5-a]pyrimidine-6-N-(2-benzothiazolyl)-carboxamide;
1-(4-chloro-phenyl)-7-oxo-1H,7H-pyrazolo[1,5-a]pyrimidine-6-N-(4-methyl-2-thiazolyl)-carboxamide;
1-(4-chloro-phenyl)-7-oxo-1H,7H-pyrazolo[1,5-a]pyrimidine-6-N-(5-chloro-2-thiazolyl)-carboxamide;
1-(4-fluoro-phenyl)-7-oxo-1H,7H-pyrazolo[1,5-a]pyrimidine-6-N-(2-pyridyl)-carboxamide, m.p. 202°–210° C. dec.;
1-(4-chloro-phenyl)-7-oxo-1H,7H-pyrazolo[1,5-a]pyrimidine-6-N-(5-chloro-2-pyridyl)-carboxamide;
1-(4-chloro-phenyl)-7-oxo-1H,7H-pyrazolo[1,5-a]pyrimidine-6-N-(4,5-dimethyl-2-thiazolyl)-carboxamide;
1-(4-nitro-phenyl)-7-oxo-1H,7H-pyrazolo[1,5-a]pyrimidine-6-N-(2-pyridyl)-carboxamide, m.p. 305°–310° C.;
1-(4-fluoro-phenyl)-7-oxo-1H,7H-pyrazolo[1,5-a]pyrimidine-6-N-(5-chloro-2-pyridyl)-carboxamide;
1-(4-fluoro-phenyl)-7-oxo-1H,7H-pyrazolo[1,5-a]pyrimidine-6-N-(4,5-dimethyl-2-thiazolyl)-carboxamide;
1-(4-fluoro-phenyl)-7-oxo-1H,7H-pyrazolo[1,5-a]pyrimidine-6-N-(6-methyl-2-pyridyl)-carboxamide;
1-(4-fluoro-phenyl)-7-oxo-1H,7H-pyrazolo[1,5-a]pyrimidine-6-N-(2-thiazolyl)-carboxamide;
1-(4-fluoro-phenyl)-7-oxo-1H,7H-pyrazolo[1,5-a]pyrimidine-6-N-(2-benzothiazolyl)-carboxamide;
1-(4-fluoro-phenyl)-7-oxo-1H,7H-pyrazolo[1,5-a]pyrimidine-6-N-(4-methyl-2-thiazolyl)-carboxamide;
1-(4-fluoro-phenyl)-7-oxo-1H,7H-pyrazolo[1,5-a]pyrimidine-6-N-(5-chloro-2-thiazolyl)-carboxamide;
1-(3-chloro-phenyl)-7-oxo-1H,7H-pyrazolo[1,5-a]pyrimidine-6-N-(2-pyridyl)-carboxamide, m.p. 284°–286° C.;
1-(3-trifluoromethyl-phenyl)-7-oxo-1H,7H-pyrazolo[1,5-a]pyrimidine-6-N-(2-pyridyl)-carboxamide, m.p. 246°–251° C.;
1-(3-chloro-phenyl)-7-oxo-1H,7H-pyrazolo[1,5-a]pyrimidine-6-N-(2-thiazolyl)-carboxamide;
1-(3-trifluoromethyl-phenyl)-7-oxo-1H,7H-pyrazolo[1,5-a]pyrimidine-6-N-(2-thiazolyl)-carboxamide;
1-(2-chloro-phenyl)-7-oxo-1H,7H-pyrazolo[1,5-a]pyrimidine-6-N-(2-pyridyl)-carboxamide;
1-(2-chloro-phenyl)-7-oxo-1H,7H-pyrazolo[1,5-a]pyrimidine-6-N-(2-thiazolyl)-carboxamide;
1-(3-methyl-phenyl)-7-oxo-1H,7H-pyrazolo[1,5-a]pyrimidine-6-N-(2-pyridyl)-carboxamide;
1-(3-chloro-phenyl)-7-oxo-1H,7H-pyrazolo[1,5-a]pyrimidine-6-N-(5-chloro-2-pyridyl)-carboxamide;
5-methyl-1-phenyl-7-oxo-1H,7H-pyrazolo[1,5-a]pyrimidine-6-N-(5-chloro-2-pyridyl)-carboxamide;
3-methyl-1-phenyl-7-oxo-1H,7H-pyrazolo[1,5-a]pyrimidine-6-N-(2-pyridyl)-carboxamide, m.p. 274°–277° C.;
3-methyl-1-phenyl-7-oxo-1H,7H-pyrazolo[1,5-a]pyrimidine-6-N-(6-methyl-2-pyridyl)-carboxamide;
3-methyl-1-phenyl-7-oxo-1H,7H-pyrazolo[1,5-a]pyrimidine-6-N-(2-thiazolyl)-carboxamide;
3-methyl-1-phenyl-7-oxo-1H,7H-pyrazolo[1,5-a]pyrimidine-6-N-(2-benzothiazolyl)-carboxamide;
3-methyl-1-phenyl-7-oxo-1H,7H-pyrazolo[1,5-a]pyrimidine-6-N-(4-methyl-2-thiazolyl)-carboxamide;
3-methyl-1-phenyl-7-oxo-1H,7H-pyrazolo[1,5-a]pyrimidine-6-N-(5-chloro-2-thiazolyl)-carboxamide;
3-methyl-1-phenyl-7-oxo-1H,7H-pyrazolo[1,5-a]pyrimidine-6-N-(5-chloro-2-pyridyl)-carboxamide;
3-methyl-1-phenyl-7-oxo-1H,7H-pyrazolo[1,5-a]pyrimidine-6-N-(4,5-dimethyl-2-thiazolyl)-carboxamide;
3-methyl-1-(4-methyl-phenyl)-7-oxo-1H,7H-pyrazolo[1,5-a]pyrimidine-6-N-(6-methyl-2-pyridyl)-carboxamide;

2-chloro-1-phenyl-7-oxo-1H,7H-pyrazolo[1,5-a]pyrimidine-6-N-(2-pyridyl)-carboxamide, m.p. 275°-278° C.;
2-chloro-1-phenyl-7-oxo-1H,7H-pyrazolo[1,5-a]pyrimidine-6-N-(6-methyl-2-pyridyl)-carboxamide;
2-chloro-1-phenyl-7-oxo-1H,7H-pyrazolo[1,5-a]pyrimidine-6-N-(2-thiazolyl)-carboxamide;
2-chloro-1-phenyl-7-oxo-1H,7H-pyrazolo[1,5-a]pyrimidine-6-N-(5-chloro-2-pyridyl)-carboxamide;
1-(4-fluoro-phenyl)-5-methyl-7-oxo-1H,7H-pyrazolo[1,5-a]pyrimidine-6-N-(2-pyridyl)-carboxamide, m.p. 252°-255° C.;
1-(4-chloro-phenyl)-3-methyl-7-oxo-1H,7H-pyrazolo[1,5-a]pyrimidine-6-N-(2-pyridyl)-carboxamide;
1-(3-chloro-phenyl)-3-methyl-7-oxo-1H,7H-pyrazolo[1,5-a]pyrimidine-6-N-(2-pyridyl)-carboxamide;
3-methyl-1-(4-methyl-phenyl)-7-oxo-1H,7H-pyrazolo[1,5-a]pyrimidine-6-N-(2-pyridyl)-carboxamide;
1-(4-fluoro-phenyl)-3-methyl-7-oxo-1H,7H-pyrazolo[1,5-a]pyrimidine-6-N-(2-thiazolyl)-carboxamide;
1-(4-chloro-phenyl)-3-methyl-7-oxo-1H,7H-pyrazolo[1,5-a]pyrimidine-6-N-(2-thiazolyl)-carboxamide;
1-(3-chloro-phenyl)-3-methyl-7-oxo-1H,7H-pyrazolo[1,5-a]pyrimidine-6-N-(2-thiazolyl)-carboxamide;
3-methyl-1-(4-methyl-phenyl)-7-oxo-1H,7H-pyrazolo[1,5-a]pyrimidine-6-N-(2-thiazolyl)-carboxamide;
1-(4-fluoro-phenyl)-3-methyl-7-oxo-1H,7H-pyrazolo[1,5-a]pyrimidine-6-N-(6-methyl-2-pyridyl)-carboxamide;
1-(4-chloro-phenyl)-3-methyl-7-oxo-1H,7H-pyrazolo[1,5-a]pyrimidine-6-N-(6-methyl-2-pyridyl)-carboxamide;
1-(4-methoxy-phenyl)-3-methyl-7-oxo-1H,7H-pyrazolo[1,5-a]pyrimidine-6-N-(6-methyl-2-pyridyl)-carboxamide;
1,5-diphenyl-7-oxo-1H,7H-pyrazolo[1,5-a]pyrimidine-6-N-(2-pyridyl)-carboxamide;
5-ethyl-1-phenyl-7-oxo-1H,7H-pyrazolo[1,5-a]pyrimidine-6-N-(2-pyridyl)-carboxamide;
1-(4-chloro-phenyl)-5-methyl-7-oxo-1H,7H-pyrazolo[1,5-a]pyrimidine-6-N-(2-pyridyl)-carboxamide;
1-(3-chloro-phenyl)-5-methyl-7-oxo-1H,7H-pyrazolo[1,5-a]pyrimidine-6-N-(2-pyridyl)-carboxamide;
5-methyl-1-(4-methyl-phenyl)-7-oxo-1H,7H-pyrazolo[1,5-a]pyrimidine-6-N-(2-pyridyl)-carboxamide;
5-methyl-1-phenyl-7-oxo-1H,7H-pyrazolo[1,5-a]pyrimidine-6-N-(6-methyl-2-pyridyl)-carboxamide;
5-methyl-1-phenyl-7-oxo-1H,7H-pyrazolo[1,5-a]pyrimidine-6-N-(2-pyrimidinyl)-carboxamide; and
3,5-dimethyl-1-phenyl-7-oxo-1H,7H-pyrazolo[1,5-a]pyrimidine-6-N-(2-pyridyl)-carboxamide.

EXAMPLE 12

1-benzyl-7-oxo-1H,7H-pyrazolo[1,5-a]pyrimidine-6-carboxylic acid, ethyl ester (3.5 g) was reacted with 2-amino-pyridine (5.2 g) in polyphosphoric acid (87 g) under stirring at 120° C. for 5 hours. After cooling, dilution with ice water and neutralization with 35% NaOH, the precipitate was filtered and washed with water: crystallization from dimethylformamide gave 1.5 g of 1-benzyl-7-oxo-1H,7H-pyrazolo[1,5-a]pyrimidine-6-N-(2-pyridyl)-carboxamide, m.p. 337°-340° C.

By proceeding analogously the following compounds were prepared:
1-benzyl-7-oxo-1H,7H-pyrazolo[B 1,5-a]pyrimidine-6-N-(3-pyridyl)-carboxamide;
1-benzyl-7-oxo-1H,7H-pyrazolo[1,5-a]pyrimidine-6-N-(5-chloro-2-pyridyl)-carboxamide;
1-benzyl-7-oxo-1H,7H-pyrazolo[1,5-a]pyrimidine-6-N-(6-methyl-2-pyridyl)-carboxamide;
1-benzyl-5-methyl-7-oxo-1H,7H-pyrazolo[1,5-a]pyrimidine-6-N-(2-pyridyl)-carboxamide;
1-benzyl-5-methyl-7-oxo-1H,7H-pyrazolo[1,5-a]pyrimidine-6-N-(5-chloro-2-pyridyl)-carboxamide;
1-benzyl-5-methyl-7-oxo-1H,7H-pyrazolo[1,5-a]pyrimidine-6-N-(3-pyridyl)-carboxamide; and
1-benzyl-5-methyl-7-oxo-1H,7H-pyrazolo[1,5-a]pyrimidine-6-N-(6-methyl-2-pyridyl)-carboxamide.

EXAMPLE 13

1-methyl-7-oxo-1H,7H-pyrazolo[1,5-a]pyrimidine-6-carboxylic acid, ethyl ester (3.4 g) was reacted with 2-amino-pyrimidine (2.9 g) in polyphosphoric acid (51 g) under stirring at 110° C. for 3 hours. After cooling, dilution with ice water and neutralization with 35% NaOH the precipitate was filtered and washed with water: crystallization from $CH_2Cl_2$/ethanol gave 2.6 g of 1-methyl-7-oxo-1H,7H-pyrazolo[1,5-a]pyrimidine-6-N-(2-pyridyl)-carboxamide, m.p. 222°-226° C., N.M.R. ($CDCl_3$-$CF_3COOD$) δ p.p.m.: 4.71 (s) (3H, $CH_3$), 6.97 (d) (1H, C-3 proton), 7.80 (m) (2H, C-4 and C-5 pyridyl protons), 8.50 (m) (3H, C-2 proton; C-3 and C-6 pyridyl protons), 9.11 (s) (1H, C-5proton).

By proceeding analogously the following compounds were prepared:
1-ethyl-7-oxo-1H,7H-pyrazolo[1,5-a]pyrimidine-6-N-(2-pyridyl)-carboxamide;
1-tert.butyl-7-oxo-1H,7H-pyrazolo[1,5-a]pyrimidine-6-N-(2-pyridyl)-carboxamide;
1-tert.butyl-5-methyl-7-oxo-1H,7H-pyrazolo[1,5-a]pyrimidine-6-N-(2-pyridyl)-carboxamide;
1,5-dimethyl-7-oxo-1H,7H-pyrazolo[1,5-a]pyrimidine-6-N-(2-pyridyl)-carboxamide, m.p. 212°-214° C.;
1-methyl-7-oxo-1H,7H-pyrazolo[1,5-a]pyrimidine-6-N-(3-pyridyl)-carboxamide;
1-methyl-7-oxo-1H,7H-pyrazolo[1,5-a]pyrimidine-6-N-(5-chloro-2-pyridyl)-carboxamide, m.p. 270°-273° C. (dec.);
1,5-dimethyl-7-oxo-1H,7H-pyrazolo[1,5-a]pyrimidine-6-N-(3-pyridyl)-carboxamide;
1-methyl-7-oxo-1H,7H-pyrazolo[1,5-a]pyrimidine-6-N-(6-methyl-2-pyridyl)-carboxamide, m.p. 225°-227° C.;
1,5-dimethyl-7-oxo-1H,7H-pyrazolo[1,5-a]pyrimidine-6-N-(5-chloro-2-pyridyl)-carboxamide, m.p. 256°-259° C.;
1,5-dimethyl-7-oxo-1H,7H-pyrazolo[1,5-a]pyrimidine-6-N-(6-methyl-2-pyridyl)-carboxamide, m.p. 220°-221° C.
1-ethyl-5-methyl-7-oxo-1H,7H-pyrazolo[1,5-a]pyrimidine-6-N-(6-methyl-2-pyridyl)-carboxamide;
1-ethyl-7-oxo-1H,7H-pyrazolo[1,5-a]pyrimidine-6-N-(5-chloro-2-pyridyl)-carboxamide;
1-tert.butyl-7-oxo-1H,7H-pyrazolo[1,5-a]pyrimidine-6-N-(6-methyl-2-pyridyl)-carboxamide;
1-ethyl-5-methyl-7-oxo-1H,7H-pyrazolo[1,5-a]pyrimidine-6-N-(2-pyridyl)-carboxamide;

1-ethyl-5-methyl-7-oxo-1H,7H-pyrazolo[1,5-a]pyrimidine-6-N-(5-chloro-2-pyridyl)-carboxamide; and
1-tert.butyl-7-oxo-1H,7H-pyrazolo[1,5-a]pyrimidine-6-N-(5-chloro-2-pyridyl)-carboxamide.

EXAMPLE 14

By proceeding according to Examples 12 and 13, using suitable hetrocyclic amines, the following compounds were prepared:
1-benzyl-7-oxo-1H,7H-pyrazolo[1,5-a]pyrimidine-6-N-(2-thiazolyl)-carboxamide;
1-benzyl-7-oxo-1H-7H-pyrazolo[1,5-a]pyrimidine-6-N-(2-benzothiazolyl)-carboxamide;
1-benzyl-7-oxo-1H,7H-pyrazolo[1,5-a]pyrimidine-6-N-(4-methyl-2-thiazolyl)-carboxamide;
1-benzyl-7-oxo-1H,7H-pyrazolo[1,5-a]pyrimidine-6-N-(5-chloro-2-thiazolyl)-carboxamide;
1-benzyl-7-oxo-1H,7H-pyrazolo[1,5-a]pyrimidine-6-N-(4,5-dimethyl-2-thiazolyl)-carboxamide;
1-methyl-7-oxo-1H,7H-pyrazolo[1,5-a]pyrimidine-6-N-(2-thiazolyl)-carboxamide, m.p. 265°–268° C. (dec.);
1-methyl-7-oxo-1H,7H-pyrazolo[1,5-a]pyrimidine-6-N-(2-benzothiazolyl)-carboxamide, m.p. 293°–298° C. (dec.);
1-methyl-7-oxo-1H,7H-pyrazolo[1,5-a]pyrimidine-6-N-(4-methyl-2-thiazolyl)-carboxamide;
1-methyl-7-oxo-1H,7H-pyrazolo[1,5-a]pyrimidine-6-N-(5-chloro-2-thiazolyl)-carboxamide;
1-methyl-7-oxo-1H,7H-pyrazolo[1,5-a]pyrimidine-6-N-(4,5-dimethyl-2-thiazolyl)-carboxamide;
1-ethyl-7-oxo-1H,7H-pyrazolo[1,5-a]pyrimidine-6-N-(2-thiazolyl)-carboxamide;
1-tert.butyl-7-oxo-1H,7H-pyrazolo[1,5-a]pyrimidine-6-N-(4,5-dimethyl-2-thiazolyl)-carboxamide;
1-tert.butyl-7-oxo-1H,7H-pyrazolo[1,5-a]pyrimidine-6-N-(2-thiazolyl)-carboxamide;
1-tert.butyl-7-oxo-1H,7H-pyrazolo[1,5-a]pyrimidine-6-N-(2-benzothiazolyl)-carboxamide;
1-tert.butyl-7-oxo-1H,7H-pyrazolo[1,5-a]pyrimidine-6-N-(4-methyl-2-thiazolyl)-carboxamide;
1-tert.butyl-7-oxo-1H,7H-pyrazolo[1,5-a]pyrimidine-6-N-(5-chloro-2-thiazolyl)-carboxamide;
1-benzyl-5-methyl-7-oxo-1H,7H-pyrazolo[1,5-a]pyrimidine-6-N-(2-thiazolyl)-carboxamide;
1-tert.butyl-5-methyl-7-oxo-1H,7H-pyrazolo[1,5-a]pyrimidine-6-N-(2-thiazolyl)-carboxamide;
1,5-dimethyl-7-oxo-1H,7H-pyrazolo[1,5-a]pyrimidine-6-N-(2-thiazolyl)-carboxamide, m.p. 243°–245° C.;
1-benzyl-5-methyl-7-oxo-1H,7H-pyrazolo[1,5-a]pyrimidine-6-N-(5-chloro-thiazolyl)-carboxamide;
1-ethyl-5-methyl-7-oxo-1H,7H-pyrazolo[1,5-a]pyrimidine-6-N-(B 5-chloro-2-thiazolyl)-carboxamide;
1,5-dimethyl-7-oxo-1H,7H-pyrazolo[1,5-a]pyrimidine-6-N-(5-chloro-2-thiazolyl)-carboxamide;
1-benzyl-5-methyl-7-oxo-1H,7H-pyrazolo[1,5-a]pyrimidine-6-N-(4,5-dimethyl-2-thiazolyl)-carboxamide;
1-ethyl-7-oxo-1H,7H-pyrazolo[1,5-a]pyrimidine-6-N-(4-methyl-2-thiazolyl)-carboxamide;
1-ethyl-5-methyl-7-oxo-1H,7H-pyrazolo[1,5-a]pyrimidine-6-N-(4,5-dimethyl-2-thiazolyl)-carboxamide;
1,5-dimethyl-7-oxo-1H,7H-pyrazolo[1,5-a]pyrimidine-6-N-(4,5-dimethyl-2-thiazolyl)-carboxamide;
1,5-dimethyl-7-oxo-1H,7H-pyrazolo[1,5-a]pyrimidine-6-N-(4-methyl-2-thiazolyl)-carboxamide;
1-benzyl-5-methyl-7-oxo-1H,7H-pyrazolo[1,5-a]pyrimidine-6-N-(4-methyl-2-thiazolyl)-carboxamide;
1-tert.butyl-5-methyl-7-oxo-1H,7H-pyrazolo[1,5-a]pyrimidine-6-N-(4-methyl-2-thiazolyl)-carboxamide;
1-benzyl-5-methyl-7-oxo-1H,7H-pyrazolo[1,5-a]pyrimidine-6-N-(2-benzothiazolyl)-carboxamide;
1,5-dimethyl-7-oxo-1H,7H-pyrazolo[1,5-a]pyrimidine-6-N-(2-benzothiazolyl)-carboxamide;
1-tert.butyl-5-methyl-7-oxo-1H,7H-pyrazolo[1,5-a]pyrimidine-6-N-(2-benzothiazolyl)-carboxamide;
1-ethyl-7-oxo-1H,7H-pyrazolo[1,5-a]pyrimidine-6-N-(4,5-dimethyl-2-thiazolyl)-carboxamide;
1-ethyl-7-oxo-1H,7H-pyrazolo[1,5-a]pyrimidine-6-N-(2-benzothiazolyl)-carboxamide;
1-ethyl-7-oxo-1H,7H-pyrazolo[1,5-a]pyrimidine-6-N-(5-chloro-2-thiazolyl)-carboxamide;
1-ethyl-5-methyl-7-oxo-1H,7H-pyrazolo[1,5-a]pyrimidine-6-N-(2-thiazolyl)-carboxamide;
1-ethyl-5-methyl-7-oxo-1H,7H-pyrazolo[1,5-a]pyrimidine-6-N-(2-benzothiazolyl)-carboxamide; and
1-ethyl-5-methyl-7-oxo-1H,7H-pyrazolo[1,5-a]pyrimidine-6-N-(4-methyl-2-thiazolyl)-carboxamide.

EXAMPLE 15

2-amino-pyridine (4.86 g), dissolved in anhydrous pyridine (10 ml) was reacted with PCl$_3$ (1.24 g) at 55° C. for 30 minutes: after cooling at 20° C. 1-phenyl-7-oxo-1H,7H-pyrazolo[1,5-a]pyrimidine-6-carboxylic acid (4 g) was added and the mixture was kept to the reflux temperature for 30 minutes. After cooling, dilution with ice water and neutralization with 37% NaOH the precipitate was filtered, washed with water and purified over a SiO$_2$ column using ethyl acetate: methanol 98:2 as eluent. Crystallization from methanol gave 2 g of 1-phenyl-7-oxo-1H,7H-pyrazolo[1,5-a]pyrimidine-6-N-(2-pyridyl)-carboxamide, m.p. 207°–210° C. dec., N.M.R. (CDCl$_3$) δ p.p.m: 6.74 (d) (1H, C-3 proton), 7.04 (m) (1H, C-5 pyridyl proton), 7.3–7.9 (m) (6H, C-4 pyridyl proton and phenyl protons), 7.94 (d) (1H, C-2 proton), 8.2–8.45 (m) (2H, C-3 and C-6 pyridyl protons), 9.25 (s) (1H, C-5 proton), 11.2 (bs) (1H, CON$\underline{H}$-).

By proceeding analogously the following compounds were prepared:
3-methyl-1-phenyl-7-oxo-1H,7H-pyrazolo[1,5-a]pyrimidine-6-N-(2-pyridyl)-carboxamide, m.p. 274°–277° C.; and
5-methyl-1-phenyl-7-oxo-1H,7H-pyrazolo[1,5-a]pyrimidine-6-N-(2-pyridyl)-carboxamide, m.p. 184°–187° C.

EXAMPLE 16

By proceeding according to Examples 3, 10 and 11, the following compounds were prepared:
1-(2-pyridyl)-7-oxo-1H,7H-pyrazolo[1,5-a]pyrimidine-6-N-(2-pyridyl)-carboxamide, m.p. 202°–204° C.;
1-(2-pyridyl)-7-oxo-1H,7H-pyrazolo[1,5-a]pyrimidine-6-N-(2-thiazolyl)-carboxamide, m.p. 218°–220° C.;
1-(2-pyridyl)-7-oxo-1H,7H-pyrazolo[1,5-a]pyrimidine-6-N-(6-methyl-2-pyridyl)-carboxamide, m.p. 212°–214° C.;
1-(2-pyridyl)-7-oxo-1H,7H-pyrazolo[1,5-a]pyrimidine-6-N-(2-benzothiazolyl)-carboxamide;
1-(3-pyridyl)-7-oxo-1H,7H-pyrazolo[1,5-a]pyrimidine-6-N-(2-pyridyl)-carboxamide; m.p. 291°–293° C.(dec.);
1-(3-pyridyl)-7-oxo-1H,7H-pyrazolo[1,5-a]pyrimidine-6-N-(2-thiazolyl)-carboxamide;
1-(3-pyridyl)-7-oxo-1H,7H-pyrazolo[1,5-a]pyrimidine-6-N-(6-methyl-2-pyridyl)-carboxamide;

1-(3-pyridyl)-7-oxo-1H,7H-pyrazolo[1,5-a]pyrimidine-6-N-(2-benzothiazolyl)-carboxamide;
1-(4-pyridyl)-7-oxo-1H,7H-pyrazolo[1,5-a]pyrimidine-6-N-(2-pyridyl)-carboxamide;
1-(4-pyridyl)-7-oxo-1H,7H-pyrazolo[1,5-a]pyrimidine-6-N-(2-thiazolyl)-carboxamide;
1-(4-pyridyl)-7-oxo-1H,7H-pyrazolo[1,5-a]pyrimidine-6-N-(6-methyl-2-pyridyl)-carboxamide;
1-(4-pyridyl)-7-oxo-1H,7H-pyrazolo[1,5-a]pyrimidine-6-N-(2-benzothiazolyl)-carboxamide;
3-methyl-1-(2-pyridyl)-7-oxo-1H,7H-pyrazolo[1,5-a]pyrimidine-6-N-(2-pyridyl)-carboxamide;
3-methyl-1-(4-pyridyl)-7-oxo-1H,7H-pyrazolo[1,5-a]pyrimidine-6-N-(2-pyridyl)-carboxamide;
5-methyl-1-(2-pyridyl)-7-oxo-1H,7H-pyrazolo[1,5-a]pyrimidine-6-N-(2-pyridyl)-carboxamide, m.p. 183°–187° C. (dec.);
5-methyl-1-(3-pyridyl)-7-oxo-1H,7H-pyrazolo[1,5-a]pyrimidine-6-N-(2-pyridyl)-carboxamide;
3-methyl-1-(2-pyridyl)-7-oxo-1H,7H-pyrazolo[1,5-a]pyrimidine-6-N-(2-thiazolyl)-carboxamide;
3-methyl-1-(4-pyridyl)-7-oxo-1H,7H-pyrazolo[1,5-a]pyrimidine-6-N-(2-thiazolyl)-carboxamide;
5-methyl-1-(2-pyridyl)-7-oxo-1H,7H-pyrazolo[1,5-a]pyrimidine-6-N-(2-thiazolyl)-carboxamide;
5-methyl-1-(3-pyridyl)-7-oxo-1H,7H-pyrazolo[1,5-a]pyrimidine-6-N-(2-thiazolyl)-carboxamide;
3-methyl-1-(2-pyridyl)-7-oxo-1H,7H-pyrazolo[1,5-a]pyrimidine-6-N-(6-methyl-2-pyridyl)-carboxamide;
3-methyl-1-(4-pyridyl)-7-oxo-1H,7H-pyrazolo[1,5-a]pyrimidine-6-N-(6-methyl-2-pyridyl)-carboxamide;
5-methyl-1-(2-pyridyl)-7-oxo-1H,7H-pyrazolo[1,5-a]pyrimidine-6-N-(6-methyl-2-pyridyl)-carboxamide;
1-(4-pyridyl)-7-oxo-1H,7H-pyrazolo[1,5-a]pyrimidine-6-N-(6-methyl-2-pyridyl)-carboxamide;
5-methyl-1-(3-pyridyl)-7-oxo-1H,7H-pyrazolo[1,5-a]pyrimidine-6-N-(6-methyl-2-pyridyl)-carboxamide;
3-methyl-1-(2-pyridyl)-7-oxo-1H,7H-pyrazolo[1,5-a]pyrimidine-6-N-(2-benzothiazolyl)-carboxamide;
3-methyl-1-(4-pyridyl)-7-oxo-1H,7H-pyrazolo[1,5-a]pyrimidine-6-N-(2-benzothiazolyl)-carboxamide;
5-methyl-1-(2-pyridyl)-7-oxo-1H,7H-pyrazolo[1,5-a]pyrimidine-6-N-(2-benzothiazolyl)-carboxamide;
5-methyl-1-(3-pyridyl)-7-oxo-1H,7H-pyrazolo[1,5-a]pyrimidine-6-N-(2-benzothiazolyl)-carboxamide;
2-methyl-1-(2-pyridyl)-7-oxo-1H,7H-pyrazolo[1,5-a]pyrimidine-6-N-(2-pyridyl)-carboxamide;
2-methyl-1-(4-pyridyl)-7-oxo-1H,7H-pyrazolo[1,5-a]pyrimidine-6-N-(2-pyridyl)-carboxamide;
1-(2-pyridyl)-7-oxo-1H,7H-pyrazolo[1,5-a]pyrimidine-6-N-(3-pyridyl)-carboxamide;
1-(3-pyridyl)-7-oxo-1H,7H-pyrazolo[1,5-a]pyrimidine-6-N-(3-pyridyl)-carboxamide;
1-(4-pyridyl)-7-oxo-1H,7H-pyrazolo[1,5-a]pyrimidine-6-N-(3-pyridyl)-carboxamide;
1-(2-pyridyl)-7-oxo-1H,7H-pyrazolo[1,5-a]pyrimidine-6-N-(5-chloro-2-pyridyl)-carboxamide, m.p. 292°–294° C. (dec.);
1-(3-pyridyl)-7-oxo-1H,7H-pyrazolo[1,5-a]pyrimidine-6-N-(5-chloro-2-pyridyl)-carboxamide;
1-(4-pyridyl)-7-oxo-1H,7H-pyrazolo[1,5-a]pyrimidine-6-N-(5-chloro-2-pyridyl)-carboxamide; and
5-methyl-1-(4-pyridyl)-7-oxo-pyrazolo[1,5-a]pyrimidine-6-N-(2-pyridyl)-carboxamide.

EXAMPLE 17

1-(4-nitro-phenyl)-7-oxo-1H,7H-pyrazolo[1,5-a]pyrimidine-6-N-(2-pyridyl)-carboxamide (4.1 g), prepared according to Example 11, was reacted with $SnCl_2.2H_2O$ (25 g) in 37% HCl (15 ml) and acetic acid (45 ml) under stirring at 60° C. for 3 hours. After cooling the precipitate was filtered and washed with water and then suspended under stirring in 2.5% aqueous $NaHCO_3$: the product was filtered, washed with water until neutral and then crystallized from $CHCl_3$-methanol to give 2.9 g of 1-(4-amino-phenyl)-7-oxo-1H,7H-pyrazolo[1,5-a]pyrimidine-6-N-(2-pyridyl)-carboxamide, m.p. 235°–245° C. dec.

By proceeding analogously the following compounds were prepared:
1-(4-amino-phenyl)-7-oxo-1H,7H-pyrazolo[1,5-a]pyrimidine-6-N-(2-thiazolyl)-carboxamide;
1-(4-amino-phenyl)-3-methyl-7-oxo-1H,7H-pyrazolo[1,5-a]pyrimidine-6-N-(2-pyridyl)-carboxamide;
1-(4-amino-phenyl)-5-methyl-7-oxo-1H,7H-pyrazolo[1,5-a]pyrimidine-6-N-(2-pyridyl)-carboxamide; and
1-(4-amino-phenyl)-2-methyl-7-oxo-1H,7H-pyrazolo[1,5-a]pyrimidine-6-N-(2-pyridyl)-carboxamide.

EXAMPLE 18

1-(4-amino-phenyl)-7-oxo-1H,7H-pyrazolo[1,5-a]pyrimidine-6-N-(2-pyridyl)-carboxamide (2 g), prepared according to Example 17, was reacted with acetic anhydride (2 ml) in dimethylformamide (30 ml) in the presence of pyridine (2 ml) at 120° C. for 1 hour. After cooling the precipitate was filtered and washed with methanol to give 1.7 g of 1-(4-acetylamino-phenyl)-7-oxo-1H,7H-pyrazolo[1,5-a]pyrimidine-6-N-(2-pyridyl)-carboxamide, m.p. 327°–332° C.

By proceeding analogously the following compounds were prepared:
1-(4-acetylamino-phenyl)-7-oxo-1H,7H-pyrazolo[1,5-a]pyrimidine-6-N-(2-thiazolyl)-carboxamide;
1-(4-acetylamino-phenyl)-3-methyl-7-oxo-1H,7H-pyrazolo[1,5-a]pyrimidine-6-N-(2-pyridyl)-carboxamide;
1-(4-acetylamino-pheny)-5-methyl-7-oxo-1H,7H-pyrazolo[1,5-a]pyrimidine-6-N-(2-pyridyl)-carboximide; and
1-(4-acetylamino-phenyl)-2-methyl-7-oxo-1H,7H-pyrazolo[1,5-a]pyrimidine-6-N-(2-pyridyl)-carboxamide.

EXAMPLE 19

By proceeding according to Example 11 the following compounds were prepared:
5-methyl-1-phenyl-1H,7H-pyrazolo[1,5-a]pyrimidine-6-N-(3-pyrazolyl)-carboxamide;
5-methyl-1-phenyl-1H,7H-pyrazolo[1,5-a]pyrimidine-6-N-(1-methyl-3-pyrazolyl)-carboxamide;
1,5-dimethyl-7-oxo-1H,7H-pyrazolo[1,5-a]pyrimidine-6-N-(3-pyridyl)-carboxamide;
1,5-dimethyl-7-oxo-1H,7H-pyrazolo[1,5-a]pyrimidine-6-N-(6-methoxy-3-pyridyl)-carboxamide;
1-methyl-7-oxo-1H,7H-pyrazolo[1,5-a]pyrimidine-6-N-(3-pyrazolyl)-carboxamide; m.p. 300°–305° C. (dec.);
1-methyl-7-oxo-1H,7H-pyrazolo[1,5-a]pyrimidine-6-N-(1-methyl-3-pyrazolyl)-carboxamide;
1,5-dimethyl-7-oxo-1H,7H-pyrazolo[1,5-a]pyrimidine-6-N-(1-methyl-3-pyrazolyl)-carboxamide;
1-phenyl-7-oxo-1H,7H-pyrazolo[1,5-a]pyrimidine-6-N-(3-pyrazolyl)-carboxamide, m.p. 296°–298° C. (dec.);

1-methyl-7-oxo-1H,7H-pyrazolo[1,5-a]pyrimidine-6-N-(5-bromo-2-pyridyl)-carboxamide, m.p. 255°–260° C. (dec.);

1-methyl-7-oxo-1H,7H-pyrazolo[1,5-a]pyrimidine-6-N-(2-pyrazinyl)-carboxamide;

1-methyl-7-oxo-1H,7-H-pyrazolo[1,5-a]pyrimidine-6-N-(2-pyrimidinyl)-carboxamide, m.p. 240°–245° C.;

1,5-dimethyl-7-oxo-1H,7H-pyrazolo[1,5-a]pyrimidine-6-N-(2-pyrimidinyl)-carboxamide;

1,5-dimethyl-7-oxo-1H,7H-pyrazolo[1,5-a]pyrimidine-6-N-(2-pyrazinyl)-carboxamide;

1-(2-pyridyl)-7-oxo-1H,7H-pyrazolo[1,5-a]pyrimidine-6-N-(2-pyrimidinyl)-carboxamide;

5-methyl-1-(2-pyridyl)-7-oxo-1H,7H-pyrazolo[1,5-a]pyrimidine-6-N-(2-pyrimidinyl)-carboxamide;

1,5-dimethyl-7-oxo-1H,7H-pyrazolo[1,5-a]pyrimidine-6-N-(3-pyrazolyl)-carboxamide;

5-methyl-1-(2-pyridyl)-7-oxo-1H,7H-pyrazolo[1,5-a]pyrimidine-6-N-(4-methyl-2-thiazolyl)-carboxamide;

1-(2-pyridyl)-7-oxo-1H,7H-pyrazolo[1,5-a]pyrimidine-6-N-(3-pyrazolyl)-carboxamide;

1-(2-pyridyl-7-oxo-1H,7H-pyrazolo[1,5-a]pyrimidine-6-N-(1-methyl-3-pyrazolyl)-carboxamide;

5-methyl-1-(2-pyridyl)-7-oxo-1H,7H-pyrazolo[1,5-a]pyrimidine-6-N-(3-pyrazolyl)-carboxamide;

5-methyl-1-(2-pyridyl)-7-oxo-1H,7H-pyrazolo[1,5-a]pyrimidine-6-N-(1-methyl-3-pyrazolyl)-carboxamide;

1-(2-pyridyl)-7-oxo-1H,7H-pyrazolo[1,5-a]pyrimidine-6-N-(2-pyrazinyl)-carboxamide;

5-methyl-1-(2-pyridyl)-7-oxo-1H,7H-pyrazolo[1,5-a]pyrimidine-6-N-(2-pyrazinyl)-carboxamide;

1-(3-pyridyl)-7-oxo-1H,7H-pyrazolo[1,5-a]pyrimidine-6-N-(3-pyrazolyl)-carboxamide;

1-(3-pyridyl)-7-oxo-1H,7H-pyrazolo[1,5-a]pyrimidine-6-N-(1-methyl-3-pyrazolyl)-carboxamide;

5-methyl-1-(3-pyridyl)-7-oxo-1H,7H-pyrazolo[1,5-a]pyrimidine-6-N-(3-pyrazolyl)-carboxamide; and 5-methyl-1-(3-pyridyl)-7-oxo-1H,7H-pyrazolo[1,5-a]pyrimidine-6-N-(1-methyl-3-pyrazolyl)-carboxamide.

EXAMPLE 20

Tablets, each weighing 100 mg and containing 50 mg of the active substance are manufactured as follows:

| Compositions (for 10,000 tablets) | |
|---|---|
| 5-methyl-1-phenyl-7-oxo-1H,7H—pyrazolo[1,5-a]pyrimidine-6-N—(2-pyridyl)-carboxamide | 500 g |
| Lactose | 710 g |
| Corn starch | 237.5 g |
| Talc powder | 35.5 g |
| Magnesium stearate | 15 g |

5-methyl-1-phenyl-7-oxo-1H,7H-pyrazolo[1,5-a]pyrimidine-6-N-(2-pyridyl)-carboxamide, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

We claim:
1. A compound of the formula (I)

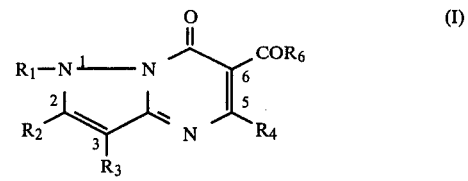

wherein
$R_1$ is (a) a 2-pyridyl, 3-pyridyl or 4-pyridyl group; (b) a phenyl ring, unsubstituted or substituted by one or two groups chosen from halogen, trihalo-$C_1$–$C_4$ alkyl, $C_1$–$C_6$ alkyl, nitro, amino and $C_2$–$C_6$ alkanoylamino; (c) benzyl; or (d) $C_1$–$C_6$ alkyl;

each of $R_2$ and $R_3$ independently is a hydrogen or a halogen atom or $C_1$–$C_6$ alkyl;

$R_4$ is hydrogen, $C_1$–$C_6$ alkyl or phenyl;

$R_5$ is (a')

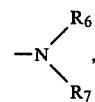

wherein each of $R_6$ and $R_7$ independently is hydrogen or $C_1$–$C_6$ alkyl, or $R_6$ and $R_7$, taken together with the nitrogen atom to which they are linked, form a morpholino, piperidino, N-pyrrolidinyl or N-piperazinyl ring, wherein the N-piperazinyl ring is unsubstituted or substituted by $C_1$–$C_6$ alkyl;

(b')

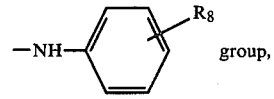

wherein $R_8$ is hydrogen, $C_1$–$C_4$ alkyl, $C_1$–$C_4$ alkoxy or halogen;

(c') —NHR$_9$, wherein $R_9$ is a 2-pyridyl, 3-pyridyl, 4-pyridyl, 2-pyrimidinyl, 2-pyrazinyl, 3-pyrazolyl, 2-thiazolyl or 2-benzothiazolyl group, each of these groups being unsubstituted or substituted by one or two groups chosen from halogen, $C_1$–$C_6$ alkyl, phenyl, hydroxy and $C_1$–$C_6$ alkoxy;

(d')

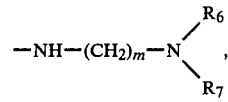

wherein m is 1, 2 or 3 and
$R_6$ and $R_7$ are as defined above; or the pharmaceutically acceptable salts thereof.

2. A compound of the formula (I), according to claim 1, wherein:
$R_1$ is 2-pyridyl; 3-pyridyl; 4-pyridyl; benzyl; $C_1$–$C_6$ alkyl; or phenyl unsubstituted or substituted by one or two groups chosen from chlorine, methyl, amino and acetylamino;

each of $R_2$ and $R_3$ independently represents hydrogen, chlorine, or a methyl group;

$R_4$ is hydrogen, $C_1$–$C_2$ alkyl or phenyl;

$R_5$ is (a'')

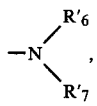

wherein each of R'$_6$ and R'$_7$ is independently hydrogen or C$_1$-C$_4$ alkyl; or R'$_6$ and R'$_7$, taken together with the nitrogen atom to which they are linked, form a morpholino, piperidino or N-piperazinyl ring, wherein the N-piperazinyl ring is unsubstituted or substituted by C$_1$-C$_4$ alkyl;

(b'')

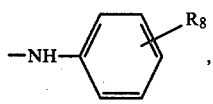

wherein R$_8$ is hydrogen, methyl, methoxy or chlorine, (c'') —NHR$_9$, wherein R$_9$ is a 2-pyridyl, 3-pyridyl, 4-pyridyl, 2-pyrimidinyl, 2-thiazolyl or 2-benzothiazolyl group, wherein all the groups are unsubstituted or substituted by one or two substituents chosen from chlorine, bromine, methyl and methoxy; or (d'')

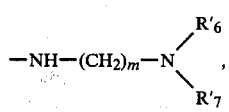

wherein m is as defined in claim (1) and R'$_6$ and R'$_7$ are as defined above; or the pharmaceutically acceptable salts thereof.

3. A compound of the formula (I), according to claim (1), wherein:

R$_1$ is 2-pyridyl; 3-pyridyl; 4-pyridyl; benzyl; or phenyl unsubstituted or substituted by one or two groups chosen from chlorine, methyl, amino and acetylamino;

each of R$_2$ and R$_3$ independently represents hydrogen, chlorine or a methyl group;

R$_4$ is hydrogen, C$_1$-C$_2$ alkyl or phenyl;

R$_5$ is (a'')

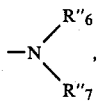

wherein each of R''$_6$ and R''$_7$ is independently hydrogen or C$_1$-C$_3$ alkyl, or R''$_6$ and R''$_7$ taken together with the nitrogen atom to which they are linked, form a morpholino, a piperidino or a N-piperazinyl ring, wherein the N-piperazinyl ring is unsubstituted or substituted by C$_1$-C$_4$ alkyl;

(b'')

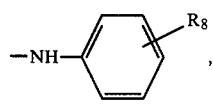

wherein R$_8$ is hydrogen, methyl methoxy or chlorine;

(c'') —NHR$_9$, wherein R$_9$ is a 2-pyridyl, 3-pyridyl, 4-pyridyl, 2-pyrimidinyl, 2-thiazolyl or 2-benzothiazolyl group wherein all the groups are unsubstituted or substituted by one or two groups chosen from chlorine, bromine, methyl and methoxy; or (d'')

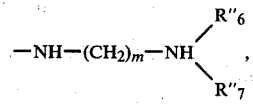

wherein m is as defined in claim (1) and R''$_6$ and R''$_7$ are as defined above; or the pharmaceutically acceptable salts thereof.

4. A compound selected from the group consisting of:
1-phenyl-7-oxo-1H,7H-pyrazolo[1,5-a]pyrimidine-6-N-(3-pyridyl)-carboxamide;
1-phenyl-7-oxo-1H,7H-pyrazolo[1,5-a]pyrimidine-6-N-(2-pyridyl)-carboxamide;
1-phenyl-7-oxo-1H,7H-pyrazolo[1,5-a]pyrimidine-6-N-(6-methyl-2-pyridyl)-carboxamide;
1-phenyl-7-oxo-1H,7H-pyrazolo[1,5-a]pyrimidine-6-N-(5-chloro-2-pyridyl)-carboxamide;
1-phenyl-7-oxo-1H,7H-pyrazolo[1,5-a]pyrimidine-6-N-(2-pyrimidinyl)-carboxamide;
3-methyl-1-phenyl-7-oxo-1H,7H-pyrazolo[1,5-a]pyrimidine-6-N-(2-pyridyl)-carboxamide;
1-phenyl-7-oxo-1H,7H-pyrazolo[1,5-a]pyrimidine-6-N-(6-methoxy-3-pyridyl)-carboxamide;
5-methyl-1-phenyl-7-oxo-1H,7H-pyrazolo[1,5-a]pyrimidine-6-N-(2-pyridyl)-carboxamide;
5-methyl-1-phenyl-7-oxo-1H,7H-pyrazolo[1,5-a]pyrimidine-6-N-(2-pyrimidinyl)-carboxamide;
3,5-dimethyl-1-phenyl-7-oxo-1H,7H-pyrazolo[1,5-a]pyrimidine-6-N-(2-pyridyl)-carboxamide;
5-ethyl-1-phenyl-7-oxo-1H,7H-pyrazolo[1,5-a]pyrimidine-6-N-(2-pyridyl)-carboxamide;
1-(3-chloro-phenyl)-7-oxo-1H,7H-pyrazolo[1,5-a]pyrimidine-6-N-(2-pyridyl)-carboxamide;
1-(3-chloro-phenyl)-5-methyl-7-oxo-1H,7H-pyrazolo[1,5-a]pyrimidine-6-N-(2-pyridyl)-carboxamide;
1-(4-chloro-phenyl)-7-oxo-1H,7H-pyrazolo[1,5-a]pyrimidine-6-N-(2-pyridyl)-carboxamide;
1-(4-chloro-phenyl)-5-methyl-7-oxo-1H,7H-pyrazolo[1,5-a]pyrimidine-6-N-(2-pyridyl)-carboxamide;
1-(4-amino-phenyl)-7-oxo-1H,7H-pyrazolo[1,5-a]pyrimidine-6-N-(2-pyridyl)-carboxamide;
1-(4-acetylamino-phenyl)-7-oxo-1H,7H-pyrazolo[1,5-a]pyrimidine-6-N-(2-pyridyl)-carboxamide;
1-(3-pyridyl)-7-oxo-1H,7H-pyrazolo[1,5-a]pyrimidine-6-N-(2-pyridyl)-carboxamide;
1-(3-pyridyl)-7-oxo-1H,7H-pyrazolo[1,5-a]pyrimidine-6-N-(6-methyl-2-pyridyl)-carboxamide;
5-methyl-1-(3-pyridyl)-7-oxo-1H,7H-pyrazolo[1,5-a]pyrimidine-6-N-(2-pyridyl)-carboxamide;
1-(3-pyridyl)-7-oxo-1H,7H-pyrazolo[1,5-a]pyrimidine-6-N-(5-chloro-2-pyridyl)-carboxamide;
1-(3-pyridyl)-7-oxo-1H,7H-pyrazolo[1,5-a]pyrimidine-6-N-(2-thiazolyl)-carboxamide;
1-(2-pyridyl)-7-oxo-1H,7H-pyrazolo[1,5-a]pyrimidine-6-N-(5-chloro-2-pyridyl)-carboxamide;

5-methyl-1-(2-pyridyl)-7-oxo-1H,7H-pyrazolo[1,5-a]pyrimidine-6-N-(2-thiazolyl)-carboxamide;
1-benzyl-7-oxo-1H,7H-pyrazolo[1,5-a]pyrimidine-6-N-(2-pyridyl)-carboxamide;
1-benzyl-5-methyl-7-oxo-1H,7H-pyrazolo[1,5-a]pyrimidine-6-N-(2-pyridyl)-carboxamide;
1-phenyl-7-oxo-1H,7H-pyrazolo[1,5-a]pyrimidine-6-N-(2-piperidino-ethyl)-carboxamide;
1-methyl-7-oxo-1H,7H-pyrazolo[1,5-a]pyrimidine-6-N-(2-pyridyl)-carboxamide;
1-ethyl-7-oxo-1H,7H-pyrazolo[1,5-a]pyrimidine-6-N-(2-pyridyl)-carboxamide;
1-(2-pyridyl)-7-oxo-1H,7H-pyrazolo[1,5-a]pyrimidine-6-N-(2-pyridyl)-carboxamide;
1-methyl-7-oxo-1H,7H-pyrazolo[1,5-a]pyrimidine-6-N-(2-thiazolyl)-carboxamide;
1-methyl-7-oxo-1H,7H-pyrazolo[1,5-a]pyrimidine-6-N-(2-benzothiazolyl)-carboxamide;
1-(2-pyridyl)-7-oxo-1H,7H-pyrazolo[1,5-a]pyrimidine-6-N-(2-thiazolyl)-carboxamide;
1-(2-pyridyl)-7-oxo-1H,7H-pyrazolo[1,5-a]pyrimidine-6-N-(2-benzothiazolyl)-carboxamide;
1-methyl-7-oxo-1H,7H-pyrazolo[1,5-a]pyrimidine-6-N-(2-piperidino-ethyl)-carboxamide;
1,5-dimethyl-7-oxo-1H,7H-pyrazolo[1,5-a]pyrimidine-6-N-(2-pyridyl)-carboxamide;
1-(4-pyridyl)-7-oxo-1H,7H-pyrazolo[1,5-a]pyrimidine-6-N-(2-pyridyl)-carboxamide;
1-methyl-7-oxo-1H,7H-pyrazolo[1,5-a]pyrimidine-6-N-(5-chloro-2-pyridyl)-carboxamide;
5-methyl-1-(2-pyridyl)-7-oxo-1H,7H-pyrazolo[1,5-a]pyrimidine-6-N-(2-pyridyl)-carboxamide;
1-phenyl-7-oxo-1H,7H-pyrazolo[1,5-a]pyrimidine-6-carboxylic acid;
5-methyl-1-phenyl-7-oxo-1H,7H-pyrazolo[1,5-a]pyrimidine-6-carboxylic acid;
1-(3-pyridyl)-7-oxo-1H,7H-pyrazolo[1,5a]pyrimidine-6-carboxylic acid; and
5-methyl-1-(3-pyridyl)-7-oxo-1H,7H-pyrazolo[1,5-a]pyrimidine-6-carboxylic acid; or the pharmaceutically acceptable salts thereof.

5. A compound of the formula (I)

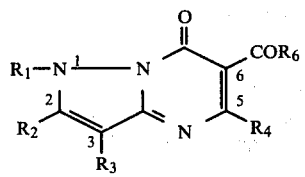

wherein:
R$_1$ is 2-pyridyl, 3-pyridyl or 4-pyridyl; benzyl; C$_1$–C$_6$ alkyl; or phenyl unsubstituted or substituted by one or two groups chosen from trifluoromethyl, halogen, C$_1$–C$_4$ alkyl, nitro, amino and acetylamino;
each of R$_2$ and R$_3$ independently is hydrogen, chlorine or a methyl group;
R$_4$ is hydrogen, C$_1$–C$_3$ alkyl or phenyl;
R$_5$ is (a)

wherein each of R$_6$ and R$_7$ is independently hydrogen or C$_1$–C$_4$ alkyl; or R$_6$ and R$_7$, taken together with the nitrogen atom to which they are linked, form a morpholino, piperidino, N-pyrrolidinyl or N-piperazinyl ring, wherein the N-piperazinyl ring is unsubstituted or substituted by C$_1$–C$_4$ alkyl;

(b)

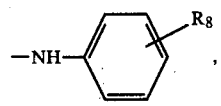

wherein R$_8$ is hydrogen, methyl, methoxy or chlorine;

(c) —NHR$_9$, wherein R$_9$ is a 2-pyridyl, 3-pyridyl, 4-pyridyl, 2-pyrimidinyl, 2-pyrazinyl, 3-pyrazolyl, 2-thiazolyl or 2-benzothiazolyl group, each of these groups being unsubstituted or substituted by one or two groups chosen from halogen, C$_1$–C$_4$ alkyl, phenyl, hydroxy and C$_1$–C$_4$ alkoxy; or (d)

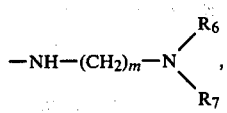

wherein m is 1, 2 or 3 and R$_6$ and R$_7$ are as defined above; or the pharmaceutically acceptable salts thereof.

6. The compound 5-methyl-1-phenyl-7-oxo-1H,7H-pyrazolo[1,5-a]pyrimidine-6-N-(2-pyridyl)-carboxamide, or the pharmaceutically acceptable salts thereof.

7. The compound 1-methyl-7-oxo-1H,7H-pyrazolo[1,5-a]pyrimidine-6-N-(2-pyridyl)-carboxamide, or the pharmaceutically acceptable salts thereof.

8. A pharmaceutical composition containing a suitable carrier and/or diluent and, as an active principle, a compound of formula (I) according to claim (1), or a pharmaceutically acceptable salt thereof.

9. A method of treatment in a human patient of inflammatory processes and pains, said method comprising administering an effective amount of a compound of claim (1).

10. A method of treatment in a human patient of inflammatory processes and pains, said method comprising administering an effective amount of a pharmaceutical composition of claim (8).

* * * * *

UNITED STATES PATENT AND TRADEMARK OFFICE
CERTIFICATE OF CORRECTION

PATENT NO. : 4,482,555

DATED : November 13, 1984

INVENTOR(S) : Gianfederico Doria, Carlo Passarotti, Ada Buttinoni

It is certified that error appears in the above-identified patent and that said Letters Patent is hereby corrected as shown below:

In the Abstract; in column 1, lines 11-19; in Claim 1 (column 32, lines 1-9); and in Claim 5 (column 35, lines 44-52); delete the substituent "$-COR_6$" from the structural formula (I) and insert therefor -- $-COR_5$ -- .

Signed and Sealed this

Fourteenth Day of May 1985

[SEAL]

Attest:

DONALD J. QUIGG

Attesting Officer

Acting Commissioner of Patents and Trademarks